United States Patent
Genet et al.

(10) Patent No.: US 6,478,827 B1
(45) Date of Patent: Nov. 12, 2002

(54) USE OF CATIONIC MONOBENZENE NITROANILINES IN THE DYEING OF KERATINOUS FIBERS, DYEING COMPOSITIONS AND DYEING PROCESSES

(75) Inventors: Alain Genet, Aulnay Sous Bois; Alain Lagrange, Coupvray, both of (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/479,239

(22) Filed: Jan. 7, 2000

(30) Foreign Application Priority Data

Jan. 8, 1999 (FR) ............................................. 9900151

(51) Int. Cl.$^7$ ................................................. A61K 7/13
(52) U.S. Cl. ..................... 8/405; 8/405; 8/409; 8/410; 8/411; 8/414; 8/415; 8/416
(58) Field of Search ........................... 8/405, 406, 410, 8/409, 411, 414, 415, 416

(56) References Cited

U.S. PATENT DOCUMENTS

| | | | |
|---|---|---|---|
| 3,817,698 A | 6/1974 | Kalopissis et al. | 8/10.1 |
| 4,018,556 A | 4/1977 | Kalopissis et al. | 8/10.1 |
| 4,888,025 A | 12/1989 | Bugaut et al. | 8/405 |
| 5,135,543 A | 8/1992 | Chan et al. | 8/405 |
| 5,139,532 A | 8/1992 | Chan et al. | 8/405 |
| 5,256,823 A | 10/1993 | Chan et al. | 564/284 |
| 5,486,629 A | * 1/1996 | Chan et al. | 552/236 |
| 5,735,910 A | 4/1998 | Lagrange et al. | 8/415 |
| 5,874,618 A | 2/1999 | Lagrange et al. | 564/305 |

FOREIGN PATENT DOCUMENTS

| | | |
|---|---|---|
| BE | 616 439 | 10/1962 |
| DE | 198 02 940 | 8/1999 |
| EP | 0 673 926 | 9/1995 |
| FR | 1 221 122 | 5/1960 |
| FR | 1 565 247 | 4/1969 |
| FR | 2 520 358 | 7/1983 |
| GB | 909 700 | 10/1962 |
| GB | 1 164 824 | 9/1969 |
| GB | 1 199 641 | 7/1970 |
| LU | 54 049 | 3/1969 |
| WO | WO 99/03836 | 1/1999 |

OTHER PUBLICATIONS

Chemical Abstracts, vol. 72, No. 2, Jan. 12, 1970, Abstract No. 4329y (JP 06 910910).

English language Derwent Abstract of DE 198 02 940.

* cited by examiner

Primary Examiner—Yogendra N. Gupta
Assistant Examiner—Eisa Elhilo
(74) Attorney, Agent, or Firm—Finnegan, Henderson, Farabow, Garrett & Dunner, L.L.P.

(57) ABSTRACT

The subject of the invention is dyeing compositions containing cationic monobenzene nitroanilines having at least one cationic charge delocalized over an unsaturated 5-membered polynitrogenous heterocycle, their use as direct dye compositions for the dyeing of keratinous substances, in particular human keratinous fibers, such as the hair, and the direct dyeing processes employing these compositions.

21 Claims, No Drawings

USE OF CATIONIC MONOBENZENE NITROANILINES IN THE DYEING OF KERATINOUS FIBERS, DYEING COMPOSITIONS AND DYEING PROCESSES

The present invention relates to dyeing compositions containing monobenzene nitroanilines having at least one cationic charge delocalized over an unsaturated 5-membered polynitrogenous heterocycle, and comprising at least one cationic group chosen from certain types of aliphatic chains, and to the use of such compositions as direct dyes in dyeing applications for keratinous substances, in particular for human keratinous fibers and especially the hair.

It is known to dye keratinous fibers, and in particular the hair, with dyeing compositions comprising direct dyes, i.e., coloring molecules having an affinity for the fibers. The dyeing process which employs them is a so-called direct coloring process, wherein the direct dyes are allowed to stand on the fibers and are then rinsed.

The colorings which result therefrom are temporary or semi-permanent colorings, because the nature of the interactions which bind the direct dyes to the keratinous fiber and their desorption from the surface and/or from the core of the fiber are responsible for their weak dyeing power and their poor ability to withstand washing operations or perspiration.

Cationic nitroanilines have certainly already been described among known direct dyes but their cationic charge is localized on the nitrogen atom of an aliphatic chain. Such nitroanilines are disclosed, for example, in U.S. Pat. Nos. 5,135,543 and 5,256,823, the disclosures of which are incorporated by However, in hair dyeing, there is a constant search for direct dyes which exhibit improved characteristics.

It is therefore after a great deal of research directed at this question that the inventors have now just discovered, entirely unexpectedly and surprisingly, that cationic monobenzene nitroanilines with at least one cationic charge delocalized over an unsaturated 5-membered polynitrogenous heterocycle and therefore comprising at least one Z cationic group, Z being chosen from quaternized aliphatic chains, aliphatic chains comprising at least one quaternized saturated ring and aliphatic chains comprising at least one quaternized unsaturated ring, are suitable for use as direct dyes in direct dyeing and, in addition, that they make it possible to obtain dyeing compositions resulting in powerful and varied colorings exhibiting excellent properties of resistance to various attacks which hair may be subject to (light, rubbing, bad weather, shampoos or perspiration) which are significantly improved with respect to those of the colors achieved with known cationic nitroanilines of the prior art, the cationic charge of which is localized on the nitrogen atom of an aliphatic chain.

Finally, these nitroanilines exhibit a better solubility in the media conventionally used for the dyeing of keratinous fibers and prove to be easy to synthesize.

These discoveries form the basis of the present invention.

A subject of the present invention is thus the use, in direct dye compositions or for the manufacture of dyeing compositions for keratinous substances and in particular for human keratinous fibers, such as the hair, of cationic monobenzene nitroanilines of following formula (I) and their acid addition salts:

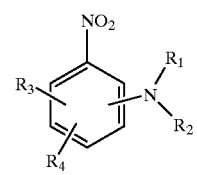

in which formula, $R_1$ and $R_2$, which can be identical or different, represent a hydrogen atom; a Z group defined below; a $(C_1-C_6)$ alkyl radical; a monohydroxy$(C_1-C_6)$alkyl radical; a polyhydroxy$(C_2-C_6)$alkyl radical; a $(C_1-C_6)$alkoxy$(C_1-C_6)$alkyl radical; an aryl radical; a benzyl radical; a cyano$(C_1-C_6)$alkyl radical; a carbamyl$(C_1-C_6)$alkyl radical; an N-$(C_1-C_6)$alkylcarbamyl$(C_1-C_6)$alkyl radical; an N,N-di$(C_1-C_6)$alkylcarbamyl$(C_1-C_6)$alkyl radical; a thiocarbamyl$(C_1-C_6)$alkyl radical; a trifluoro$(C_1-C_6)$alkyl radical; a sulpho$(C_1-C_6)$alkyl radical; a $(C_1-C_6)$alkylcarboxy$(C_1-C_6)$alkyl radical; a $(C_1-C_6)$alkylsulphinyl$(C_1-C_6)$alkyl radical; an aminosulphonyl$(C_1-C_6)$alkyl radical; an N—Z-aminosulphonyl$(C_1-C_6)$alkyl radical; an N-$(C_1-C_6)$alkylaminosulphonyl$(C_1-C_6)$alkyl radical; an N,N-di$(C_1-C_6)$alkylaminosulphonyl$(C_1-C_6)$alkyl radical; a $(C_1-C_6)$alkylcarbonyl$(C_1-C_6)$alkyl radical; an amino$(C_1-C_6)$alkyl radical, the alkyl of which is unsubstituted or substituted by one or more hydroxyl radicals; or an amino$(C_1-C_6)$alkyl radical, the alkyl of which is unsubstituted or substituted by one or more hydroxyl radicals and the amine of which is substituted by one or two identical or different radicals which may together form, with the nitrogen atom to which they are attached, a carbonaceous 5- or 6-membered ring or a 5- or 6-membered ring comprising one or more heteroatoms, or which are chosen from alkyl, monohydroxy$(C_1-C_6)$alkyl, polyhydroxy$(C_2-C_6)$alkyl, $(C_1-C_6)$alkylcarbonyl, carbamyl, N-$(C_1-C_6)$alkylcarbamyl or N,N-di$(C_1-C_6)$alkylcarbamyl, $(C_1-C_6)$alkylsulphonyl, formyl, trifluoro$(C_1-C_6)$alkylcarbonyl, $(C_1-C_6)$alkylcarboxyl or thiocarbamyl radicals, or from a Z group defined below;

$R_3$ and $R_4$, which can be identical or different, represent a hydrogen atom; a halogen atom; a Z group defined below; a $(C_1-C_6)$alkylcarbonyl radical; an amino$(C_1-C_6)$alkylcarbonyl radical; an N—Z-amino$(C_1-C_6)$alkylcarbonyl radical; an N-$(C_1-C_6)$alkylamino$(C_1-C_6)$alkylcarbonyl radical; an N,N-di$(C_1-C_6)$alkylamino$(C_1-C_6)$alkylcarbonyl radical; an amino$(C_1-C_6)$alkylcarbonyl$(C_1-C_6)$alkyl radical; an N—Z-amino$(C_1-C_6)$alkylcarbonyl$(C_1-C_6)$alkyl radical; an N-$(C_1-C_6)$alkylamino$(C_1-C_6)$alkylcarbonyl$(C_1-C_6)$alkyl radical; an N,N-di$(C_1-C_6)$alkylamino-$(C_1-C_6)$alkylcarbonyl$(C_1-C_6)$alkyl radical; a carboxyl radical; a $(C_1-C_6)$alkylcarboxyl radical; a $(C_1-C_6)$alkylsulphonyl radical; an aminosulphonyl radical; an N—Z-aminosulphonyl radical; an N-$(C_1-C_6)$alkylaminosulphonyl radical; an N,N-di$(C_1-C_6)$alkylaminosulphonyl radical; an aminosulphonyl$(C_1-C_6)$alkyl radical; an N—Z-aminosulphonyl$(C_1-C_6)$alkyl radical; an N-$(C_1-C_6)$alkylaminosulphonyl$(C_1-C_6)$alkyl radical; an N,N-di$(C_1-C_6)$alkylaminosulphonyl$(C_1-C_6)$alkyl radical; a carbamyl radical; an N-$(C_1-C_6)$alkylcarbamyl radical; an N,N-di$(C_1-C_6)$alkylcarbamyl radical; a carbamyl$(C_1-C_6)$alkyl radical; an N-$(C_1-C_6)$alkylcarbamyl ($C_1$–$C_6$)alkyl radical; an N,N-di($C_1$–$C_6$)alkylcarbamyl ($C_1$–$C_6$)alkyl radical; a ($C_1$–$C_6$)alkyl radical; a monohydroxy($C_1$–$C_6$)alkyl radical; a polyhydroxy ($C_2$–$C_6$)alkyl radical; a ($C_1$–$C_6$)alkoxy($C_1$–$C_6$)alkyl radical; a trifluoro($C_1$–$C_6$)alkyl radical; a cyano radical; an $OR_5$ or —$SR_5$ group defined below; or an amino($C_1$–$C_6$)alkyl radical, the alkyl of which is unsubstituted or substituted by one or more hydroxyl radicals and the amine of which is unsubstituted or substituted by one or two identical or different radicals which may together form, with the nitrogen atom to which they are attached, a carbonaceous 5- or 6-membered ring or a 5- or 6-membered ring comprising one or more heteroatoms, or which are chosen from ($C_1$–$C_6$)alkyl, monohydroxy($C_1$–$C_6$)alkyl, polyhydroxy($C_2$–$C_6$)alkyl, ($C_1$–$C_6$)alkylcarbonyl, carbamyl, N-($C_1$–$C_6$)alkylcarbamyl or N,N-di($C_1$–$C_6$) alkylcarbamyl, ($C_1$–$C_6$)alkylsulphonyl, formyl, trifluoro($C_1$–$C_6$)alkylcarbonyl, ($C_1$–$C_6$)alkylcarboxyl or thiocarbamyl radicals, or from a Z group defined below;

$R_5$ denotes a hydrogen atom; a ($C_1$–$C_6$)alkyl radical; a monohydroxy($C_1$–$C_6$)alkyl radical; a polyhydroxy ($C_2$–$C_6$)alkyl radical; a Z group; a ($C_1$–$C_6$)alkoxy ($C_1$–$C_6$)alkyl radical; an aryl radical; a benzyl radical; a carboxy($C_1$–$C_6$)alkyl radical; a ($C_1$–$C_6$)alkylcarboxy ($C_1$–$C_6$)alkyl radical; a cyano($C_1$–$C_6$)alkyl radical; a carbamyl($C_1$–$C_6$)alkyl radical; an N-($C_1$–$C_6$) alkylcarbamyl($C_1$–$C_6$)alkyl radical; an N,N-di($C_1$–$C_6$) alkylcarbamyl($C_1$–$C_6$)alkyl radical; a trifluoro($C_1$–$C_6$) alkyl radical; an aminosulphonyl($C_1$–$C_6$)alkyl radical; an N—Z-aminosulphonyl($C_1$–$C_6$)alkyl radical; an N-($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$) alkylcarbonyl($C_1$–$C_6$)alkyl radical; an amino($C_1$–$C_6$) alkyl radical, the alkyl of which is unsubstituted or substituted by one or more hydroxyl radicals; or an amino($C_1$–$C_6$)alkyl radical, the alkyl of which is unsubstituted or substituted by one or more hydroxyl radicals and the amine of which is substituted by one or two identical or different radicals which may together form, with the nitrogen atom to which they are attached, a carbonaceous 5- or 6-membered ring or a 5- or 6-membered ring comprising one or more heteroatoms, or which are chosen from ($C_1$–$C_6$)alkyl, monohydroxy($C_1$–$C_6$)alkyl, polyhydroxy($C_2$–$C_6$)alkyl, ($C_1$–$C_6$)alkylcarbonyl, formyl, trifluoro($C_1$–$C_6$) alkylcarbonyl, ($C_1$–$C_6$)alkylcarboxyl, carbamyl, N-($C_1$–$C_6$)alkylcarbamyl, N,N-di($C_1$–$C_6$) alkylcarbamyl, thiocarbamyl or ($C_1$–$C_6$)alkylsulphonyl radicals, or from a Z group defined below;

Z is chosen from the unsaturated cationic groups of following formulae (II) and (III) and the saturated cationic groups of following formula (IV):

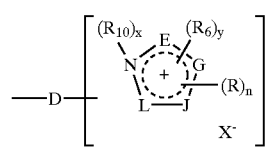

(II)

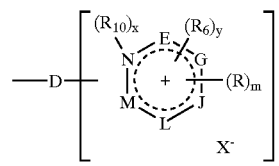

(III)

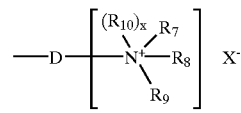

(IV)

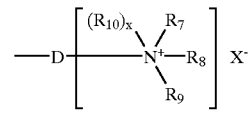

(IV)

in which:

D is a linking arm which represents a linear or branched alkyl chain preferably comprising from 1 to 14 carbon atoms which can be interrupted by one or more heteroatoms, such as oxygen, sulphur or nitrogen atoms, and which can be substituted by one or more hydroxyl or ($C_1$–$C_6$)alkoxy radicals and which can carry one or more ketone functional groups;

a the E, G, J, L and M vertices, which are identical or different, represent a carbon, oxygen, sulphur or nitrogen atom;

n is an integer ranging from 0 to 4;

m is an integer ranging from 0 to 5;

the R radicals, which are identical or different, represent a second Z group identical to or different from the first Z group; a halogen atom; a hydroxyl radical; a ($C_1$–$C_6$)alkyl radical; a monohydroxy($C_1$–$C_6$)alkyl radical; a polyhydroxy($C_2$–$C_6$)alkyl radical; a nitro radical; a cyano radical; a cyano($C_1$–$C_6$)alkyl radical; a ($C_1$–$C_6$)alkoxy radical; a tri($C_1$–$C_6$)alkylsilyl ($C_1$–$C_6$)alkyl radical; an amido radical; a formyl radical; a carboxyl radical; a ($C_1$–$C_6$)alkylcarbonyl radical; a thio radical; a thio($C_1$–$C_6$)alkyl radical; a ($C_1$–$C_6$)alkylthio radical; an amino radical; an amino radical protected by a ($C_1$–$C_6$)alkylcarbonyl, carbamyl or ($C_1$–$C_6$)alkylsulphonyl radical; or an NHR" or NR"R'" group in which R" and R'", which are identical or different, represent a ($C_1$–$C_6$)alkyl radical, a monohydroxy($C_1$–$C_6$)alkyl radical or a polyhydroxy($C_2$–$C_6$)alkyl radical;

$R_6$ represents a ($C_1$–$C_6$)alkyl radical; a monohydroxy ($C_1$–$C_6$)alkyl radical; a polyhydroxy($C_2$–$C_6$)alkyl radical; a cyano($C_1$–$C_6$)alkyl radical; a tri($C_1$–$C_6$) alkylsilyl($C_1$–$C_6$)alkyl radical; a ($C_1$–$C_6$)alkoxy ($C_1$–$C_6$)alkyl radical; a carbamyl($C_1$–$C_6$)alkyl radical; a ($C_1$–$C_6$)alkylcarboxy($C_1$–$C_6$)alkyl radical; a benzyl radical; or a second Z group identical to or different from the first Z group;

$R_7$, $R_8$ and $R_9$, which are identical or different, represent a ($C_1$–$C_6$)alkyl radical; a monohydroxy($C_1$–$C_6$) alkyl radical; a polyhydroxy($C_2$–$C_6$)alkyl radical; a ($C_1$–$C_6$)alkoxy($C_1$–$C_6$)alkyl radical; a cyano($C_1$–$C_6$) alkyl radical; an aryl radical; a benzyl radical; an amido($C_1$–$C_6$)alkyl radical; a tri($C_1$–$C_6$)alkylsilyl ($C_1$–$C_6$)alkyl radical; or an amino($C_1$–$C_6$)alkyl radical, the amine of which is protected by a ($C_1$–$C_6$)

alkylcarbonyl, carbamyl or $(C_1-C_6)$alkylsulphonyl radical; two of the $R_7$, $R_8$ and $R_9$ radicals can also together form, with the nitrogen atom to which they are attached, a saturated carbonaceous 5- or 6-membered ring or a saturated 5- or 6-membered ring which can comprise one or more heteroatoms, such as, for example, a pyrrolidine ring, a piperidine ring, a piperazine ring or a morpholine ring, it being possible for the said ring to be substituted or unsubstituted by a halogen atom, a hydroxyl radical, a $(C_1-C_6)$alkyl radical, a monohydroxy$(C_1-C_6)$alkyl radical, a polyhydroxy$(C_2-C_6)$alkyl radical, a nitro radical, a cyano radical, a cyano$(C_1-C_6)$alkyl radical, a $(C_1-C_6)$alkoxy radical, a tri$(C_1-C_6)$alkylsilyl$(C_1-C_6)$alkyl radical, an amido radical, a formyl radical, a carboxyl radical, a keto$(C_1-C_6)$alkyl radical, a thio radical, a thio$(C_1-C_6)$alkyl radical, a $(C_1-C_6)$alkylthio radical, an amino radical or an amino radical protected by a $(C_1-C_6)$alkylcarbonyl, carbamyl or $(C_1-C_6)$alkylsulphonyl radical; one of the $R_7$, $R_8$ and $R_9$ radicals can also represent a second Z group identical to or different from the first Z group;

$R_{10}$ represents a $(C_1-C_6)$alkyl radical; a monohydroxy $(C_1-C_6)$alkyl radical; a polyhydroxy$(C_2-C_6)$alkyl radical; an aryl radical; a benzyl radical; an amino $(C_1-C_6)$alkyl radical; an amino$(C_1-C_6)$alkyl radical, the amine of which is protected by a $(C_1-C_6)$alkylcarbonyl, carbamyl or $(C_1-C_6)$alkylsulphonyl radical; a carboxy$(C_1-C_6)$alkyl radical; a cyano $(C_1-C_6)$alkyl radical; a carbamyl$(C_1-C_6)$alkyl radical; a trifluoro$(C_1-C_6)$alkyl radical; a tri$(C_1-C_6)$alkylsilyl$(C_1-C_6)$alkyl radical; a sulphonamido $(C_1-C_6)$alkyl radical; a $(C_1-C_6)$alkylcarboxy $(C_1-C_6)$alkyl radical; a $(C_1-C_6)$alkylsulphinyl $(C_1-C_6)$alkyl radical; a $(C_1-C_6)$alkylsulphonyl $(C_1-C_6)$alkyl radical; a $(C_1-C_6)$alkylketo$(C_1-C_6)$alkyl radical; an N-$(C_1-C_6)$alkylcarbamyl$(C_1-C_6)$alkyl radical; or an N-$(C_1-C_6)$alkylsulphonamido $(C_1-C_6)$alkyl radical;

x and y are integers equal to 0 or 1; with the following conditions:
in the unsaturated cationic groups of formula (III):
when x=0, the D linking arm is attached to the nitrogen atom,
when x=1, the D linking arm is attached to one of the E, G, J or L vertices,
y can take the value 1 only:
1) when the E, G, J and L vertices simultaneously represent a carbon atom and when the $R_6$ radical is carried by the nitrogen atom of the unsaturated ring; or else
2) when at least one of the E, G, J and L vertices represents a nitrogen atom to which the $R_6$ radical is attached;
in the unsaturated cationic groups of formula (III):
when x=0, the D linking arm is attached to the nitrogen atom,
when x=1, the D linking arm is attached to one of the E, G, J, L or M vertices,
y can take the value 1 only when at least one of the E, G, J, L and M vertices represents a divalent atom and when the $R_6$ radical is carried by the nitrogen atom of the unsaturated ring;
in the cationic groups of formula (IV):
when x=0, then the D linking arm is attached to the nitrogen atom carrying the $R_7$ to $R_9$ radicals,
when x=1, then two of the $R_7$ to $R_9$ radicals jointly form, with the nitrogen atom to which they are attached, a saturated 5- or 6-membered ring as defined above and the D linking arm is carried by a carbon atom of the said saturated ring;
$X^-$ represents a monovalent or divalent anion and is preferably chosen from a halogen atom, such as chlorine, bromine, fluorine or iodine, a hydroxide, a hydrogen sulphate or a $(C_1-C_6)$alkyl sulphate, such as, for example, a methyl sulphate or an ethyl sulphate;
it being understood:
that the number of Z unsaturated cationic groups of formula (II) in which at least one of the E, G, J and L vertices represents a nitrogen atom is at least equal to 1, and
that, when one and only one of the $R_1$ or $R_2$ or $R_5$ radicals denotes a Z group in which the D linking arm represents an alkyl chain comprising a ketone functional group, then the ketone functional group is not directly attached to the nitrogen atom of the $NR_1R_2$ group or to the oxygen atom of the $OR_5$ group when $R_1$ or $R_2$ represents $OR_5$.

The alkyl and alkoxy radicals mentioned above in the formulae (I), (II), (III) and (IV) can be linear or branched.

The cationic monobenzene nitroanilines of formula (I) can optionally be salified by strong inorganic acids, such as HCl, HBr or $H_2SO_4$, or organic acids, such as acetic, lactic, tartaric, citric or succinic acid.

Mention may in particular be made, among the rings of the Z unsaturated groups of above formula (II), by way of example, of the pyrrole, imidazole, pyrazole, oxazole, thiazole and triazole rings.

Mention may in particular be made, among the rings of the Z unsaturated groups of above formula (III), by way of example, of the pyridine, pyrimidine, pyrazine, oxazine and triazine rings.

Mention may in particular be made, among the cationic monobenzene nitroanilines of above formula (I), of the following compounds:

3-(3-(4,5-dichloro-2-nitrophenylamino)propyl)-1-methyl-3H-imidazol-1-ium methyl sulphate, 3-(3-(4-chloro-5-methoxy-2-nitrophenylamino)propyl)-1-methyl-3H-imidazol-1-ium methyl sulphate, 3-(3-(4-chloro-5-methylsulphanyl-2-nitrophenylamino) propyl)-1-methyl-3H-imidazol-1-ium methyl sulphate, 1,3-dimethyl-2-(3-methylamino-4-nitrophenylsulphanyl)-3H-imidazol-1-ium methyl sulphate, 1-{2-(5-(2-hydroxyethylamino)-2-methyl-4-nitrophenoxy)ethyl}-3-methyl-3H-imidazol-1-ium bromide, 3-(3-(4-methoxy-2-nitrophenylamino)propyl)-1-methyl-3H-imidazol-1-ium methyl sulphate hydrate, 3-{3-(4-(2-hydroxyethoxy)-2-nitrophenylamino)propyl}-1-methyl-3H-imidazol-1-ium methyl sulphate, 3-methyl-1-(2-(4-nitrophenylamino)ethyl)-3H-imidazol-1-ium bromide, 1-methyl-3-(3-(4-nitrophenylamino)propyl)-3H-imidazol-1-ium methyl sulphate, 1-(3-(2-amino-5-nitrophenoxy)propyl)-3-methyl-3H-imidazol-1-ium chloride hydrochloride, 3-(3-(4,5-dichloro-2-nitrophenylamino)propyl)-1-(3-(trimethylsilanyl)propyl)-3H-imidazol-1-ium chloride hydrate, 1-(3-(2-amino-5-nitrophenoxy)propyl)-2-methyl-2H-pyrazol-1-ium bromide, 1-methyl-3-(3-(2-nitrophenylamino)propyl)-3H-imidazol-1-ium methyl sulphate, 1-(3-chloropropyl)-3-(3-(4-nitrophenylamino)propyl)-3H-imidazol-1-ium chloride, 1-(2-hydroxyethyl)-3-(3-(4-nitrophenylamino)propyl)-3H-imidazol-1-ium chloride, 3-(3-(4-benzyloxy-2-nitrophenylamino)propyl)-1-methyl-3H-imidazol-1-ium methyl sulphate, 3-(3-(2-cyano-4-nitrophenylamino)propyl)-1-methyl-3H-imidazol-1-ium methyl sulphate, 1-methyl-3-(3-(2-methyl-4-nitrophenylamino)propyl)-3H-imidazol-1-ium methyl sulphate, 3-(3-(2-fluoro-4-nitrophenylamino)propyl)-1-methyl-3H-imidazol-1-ium methyl sulphate, 1-(2-(2-methoxy-4-nitrophenylamino)ethyl)-3-methyl-3H-imidazol-1-ium bromide, 3-(3-(3-hydroxy-4-nitrophenylamino)propyl)-1-methyl-3H-imidazol-1-ium methyl sulphate, 3-(3-(2-chloro-4-nitrophenylamino)propyl)-1-methyl-3H-imidazol-1-ium methyl sulphate, 2-methyl-1-(2-(4-nitrophenylamino)ethyl)-2H-pyrazol-1-ium bromide, 1-(3-bromo-2-hydroxypropyl)-3-(3-(4-nitrophenylamino)propyl)-3H-imidazol-1-ium bromide, 1-(3-trimethylammonio-2-hydroxypropyl)-3-(3-(4-nitrophenylamino)propyl)-3H-1-ium dichloride, diethyl(2-hydroxyethyl)(4-(4-nitrophenylamino)pentyl) ammonium chloride, 3-(3-(4-chloro-2-nitrophenylamino)propyl)-1-methyl-3H-imidazol-1-ium methyl sulphate, 3-(3-(2-chloro-6-nitrophenylamino)propyl)-1-methyl-3H-imidazol-1-ium methyl sulphate, 1-methyl-3-(2-(4-nitrophenylamino)butyl)-3H-imidazol-1-ium chloride, 3-methyl-1-(2-methyl-2-(4-nitrophenylamino)propyl)-3H-imidazol-1-ium chloride, 1-{2-((2-(3-methyl-3H-imidazol-1-io)ethyl)(4-nitrophenyl)amino)ethyl}-3-methyl-3H-imidazol-1-ium dichloride, and, more preferably among these, the compounds of following formulae (I)$_1$ to (I)$_{11}$ are chosen:

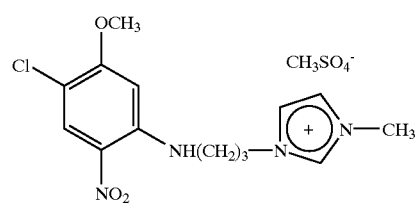

i.e., 3-(3-(4-chloro-5-methoxy-2-nitrophenylamino)propyl)-1-methyl-3H-imidazol-1-ium methyl sulphate,

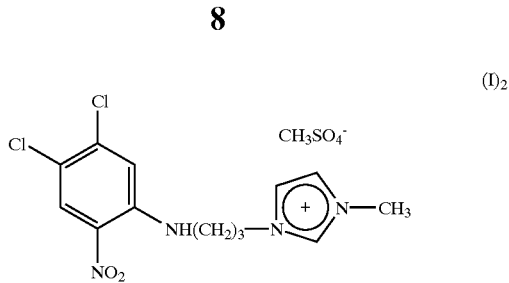

i.e., 3-(3-(4,5-dichloro-2-nitrophenylamino)propyl)-1-methyl-3H-imidazol-1-ium methyl sulphate,

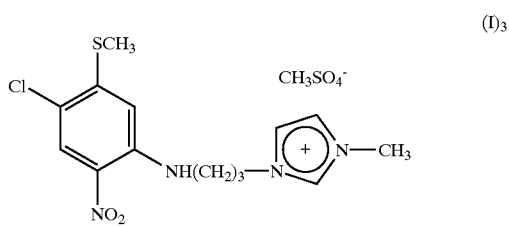

i.e., 3-(3-(4-chloro-5-methylsulphanyl-2-nitrophenylamino)propyl)-1-methyl-3H-imidazol-1-ium methyl sulphate,

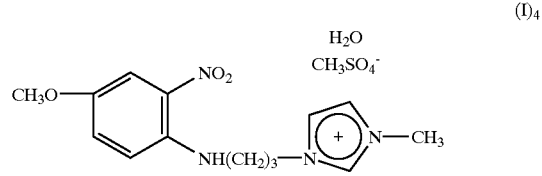

i.e., 3-(3-(4-methoxy-2-nitrophenylamino)propyl)-1-methyl-3H-imidazol-1-ium methyl sulphate hydrate,

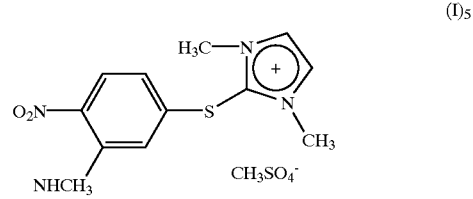

i.e., 1,3-dimethyl-2-(3-methylamino-4-nitrophenylsulphanyl)-3H-imidazol-1-ium methyl sulphate,

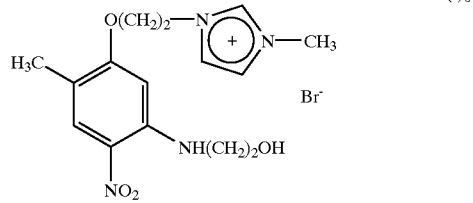

i.e., 1-{2-(5-(2-hydroxyethylamino)-2-methyl-4-nitrophenoxy)ethyl}-3-methyl-3H-imidazol-1-ium bromide,

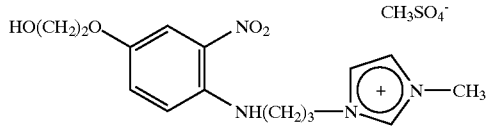

i.e., 3-{3-(4-(2-hydroxyethoxy)-2-nitrophenylamino)propyl}-1-methyl-3H-imidazol-1-ium methyl sulphate,

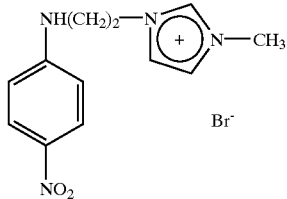

i.e., 3-methyl-1-(2-(4-nitrophenylamino)ethyl)-3H-imidazol-1-ium bromide,

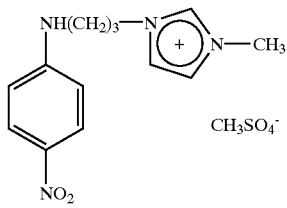

i.e., 1-methyl-3-(3-(4-nitrophenylamino)propyl)-3H-imidazol-1-ium methyl sulphate,

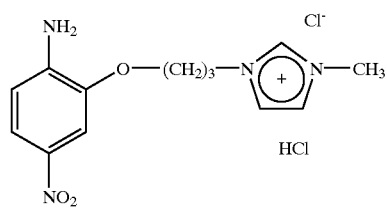

i.e., 1-(3-(2-amino-5-nitrophenoxy)propyl)-3-methyl-3H-imidazol-1-ium chloride hydrochloride,

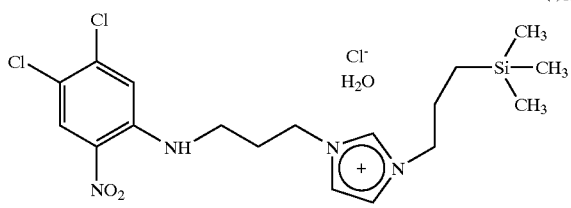

i.e., 3-(3-(4,5-dichloro-2-nitrophenylamino)propyl)-1-(3-(trimethylsilanyl)propyl)-3H-imidazol-1-ium chloride hydrate.

The cationic monobenzene nitroanilines of formula (I) in accordance with the invention can be easily obtained according to methods generally well known in the state of the art for the preparation of quaternized amines, for example:

in one step, by condensation of a nitroaniline comprising a haloalkyl radical with a compound carrying a tertiary amine radical or by condensation of a nitroaniline comprising a tertiary amine radical with a compound carrying a haloalkyl radical;

or, in two steps, by condensation of a nitroaniline comprising a haloalkyl radical with a compound carrying a secondary amine or by condensation of an ortho- or para-halonitrobenzene with a (disubstituted amino) alkylamine, followed by quaternization with an alkylating agent.

The quaternization stage is generally, for convenience, the final stage of the synthesis but can take place earlier in the sequence of reactions resulting in the preparation of the compounds of formula (I).

Another subject of the invention is a dyeing composition for keratinous substances, characterized in that it comprises, in a medium appropriate for dyeing, an effective amount of at least one cationic monobenzene nitroaniline of formula (I) described above.

Another subject of the invention is a composition for the direct dyeing of human keratinous fibers, such as the hair, characterized in that it comprises, in a medium appropriate for dyeing, an effective amount of at least one cationic monobenzene nitroaniline as defined above by the formula (I).

Another subject of the invention is the use of the cationic monobenzene nitroanilines of formula (I) as direct dyes in or for the preparation of dyeing compositions for keratinous substances.

However, other characteristics, aspects and advantages of the invention will become even more clearly apparent on reading the description which will follow and various concrete but in no way limiting examples intended to illustrate it.

The cationic monobenzene nitroaniline(s) of formula (I) in accordance with the invention and/or their addition salts with an acid preferably represent from 0.005 to 12% by weight approximately of the total weight of the dyeing composition and more preferably still from 0.05 to 6% by weight approximately of this weight.

The cationic monobenzene nitroanilines of formula (I) can also be used, in the well known processes for oxidation dyeing using oxidation dyes (oxidation dye precursors and, optionally, couplers), to shade or enrich with highlights the colors obtained with the oxidation dyes.

The dyeing composition according to the invention can also comprise, in order to widen the palette of shades and to obtain varied hues, in addition to the cationic monobenzene nitroanilines of formula (I), other direct dye(s) conventionally used and in particular nitrobenzene dyes other than the cationic monobenzene nitroanilines of formula (I) according to the present invention, such as nitrophenylenediamines, nitrodiphenylamines, nitrophenol ethers or nitrophenols, nitropyridines, anthraquinone dyes, mono- or diazo, triarylmethane, azine, acridine and xanthene dyes, or metal complex dyes.

The proportion of all these other additional direct dyes can vary from approximately 0.05 to 10% by weight with respect to the total weight of the dyeing composition.

The medium appropriate for dyeing (or vehicle) is generally composed of water or of a mixture of water and of at least one organic solvent, in order to dissolve the compounds which would not be sufficiently soluble in water. Mention may be made, for example, as organic solvent, of lower $C_1$–$C_4$ alkanols, such as ethanol and isopropanol, glycerol, glycols and glycol ethers, such as 2-butoxyethanol, propylene glycol or propylene glycol monomethyl ether, and aromatic alcohols, such as benzyl alcohol or phenoxyethanol, the analogous products and their mixtures.

The solvents can be present in proportions preferably ranging from 1 to 40% by weight with respect to the total weight of the dyeing composition and more preferably still from 5 to 30% by weight approximately.

Fatty amides, such as the mono- and diethanolamides of the acids derived from copra, of lauric acid or of oleic acid, can also be added to the composition according to the invention at concentrations ranging from approximately 0.05 to 10% by weight.

Surface-active agents well known in the state of the art and of anionic, cationic, nonionic, amphoteric or zwitterionic type or their mixtures can also be added to the composition according to the invention, preferably in a proportion ranging from approximately 0.1 to 50% by weight and advantageously from approximately 1 to 20% by weight with respect to the total weight of the composition.

Thickening agents can also be used in a proportion ranging from approximately 0.2 to 5%.

The dyeing composition can additionally comprise various conventional adjuvants, such as antioxidizing agents, fragrances, sequestering agents, dispersing agents, hair conditioning agents, preserving agents, opacifying agents and any other adjuvant commonly used in dyeing keratinous substances.

Of course, a person skilled in the art will take care to choose the optional additional compound or compounds mentioned above so that the advantageous properties intrinsically attached to the dyeing composition according to the invention are not, or not substantially, detrimentally affected by the envisaged addition or additions.

The dyeing composition according to the invention can be formulated at acidic, neutral or alkaline pH, it being possible for the pH to vary from 3 to 12 approximately and preferably from 5 to 11 approximately. It can be adjusted to the desired value by means of acidifying or basifying agents or of buffers commonly used in dyeing keratinous substances.

The acidifying agents are conventionally inorganic or organic acids, such as, for example, hydrochloric acid, orthophosphoric acid or sulphuric acid, carboxylic acids, such as acetic acid, tartaric acid, citric acid or lactic acid, and sulphonic acids.

Mention may be made, among buffers, of, for example, potassium dihydrogen phosphate/sodium hydroxide.

Mention may be made, among basifying agents, by way of example, of aqueous ammonia, alkaline carbonates, alkanolamines, such as mono-, di- and triethanolamines, and their derivatives, sodium hydroxide, potassium hydroxide and the compounds of formula:

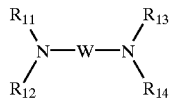

in which W is a propylene residue optionally substituted by a hydroxyl group or a ($C_1$–$C_4$)alkyl radical and $R_{11}$, $R_{12}$, $R_{13}$ and $R_{14}$, simultaneously or independently of one another, represent a hydrogen atom or a ($C_1$–$C_6$)alkyl or hydroxy ($C_1$–$C_6$)alkyl radical.

The composition applied to the hair can be provided in various forms, such as in the form of a liquid, cream or gel or in any other form appropriate for carrying out dyeing of keratinous substances. In particular, it can be packaged under pressure in an aerosol can in the presence of a propellant and can form a foam.

Another subject-matter of the present invention is a process for dyeing keratinous fibers, in particular human keratinous fibers, such as the hair, by direct coloring, which comprises the step of allowing a dyeing composition comprising at least one cationic monobenzene nitroaniline of formula (I) to act on dry or wet keratinous fibers. The composition according to the invention can be used as a leave-in composition, that is to say that, after application of the composition to the fibers, drying is carried out without intermediate rinsing.

In the other applicational methods, the composition is allowed to act on the fibers for an exposure time varying from 3 to 60 minutes approximately, preferably from 5 to 45 minutes approximately, rinsing is carried out, washing is optionally carried out, rinsing is then again carried out, and drying is carried out.

Concrete examples illustrating the invention will now be given.

PREPARATION EXAMPLES

Example 1

Preparation of the Compound of Formula (I)$_2$ 3-(3-(4,5-Dichloro-2-nitrophenylamino)propyl)-1-methyl-3H-imidazol-1-ium Methyl Sulphate 1st Stage:

Synthesis of (4,5-Dichloro-2-nitrophenyl)(3-(imidazol-1-yl)propyl)amine

A mixture of 90.6 g (0.4 mol) of 1,2,4-trichloro-5-nitrobenzene (RN 89-69-0), 50.1 g (0.45 mol) of 3-(imidazol-1-yl)propylamine (RN 5036-48-6) and 62.7 ml (0.45 mol) of triethylamine in 100 ml of 1,2-dimethoxyethane was heated with stirring for 3 hours at reflux.

The mixture was poured into 1.5 l of ice-cold water and the crystallized precipitate was filtered off, reslurried in water and then in isopropyl alcohol and dried under vacuum at 40° C. over phosphorus pentoxide. 54.5 g of orange-yellow crystals were obtained, which crystals, after purification by recrystallization from refluxing ethyl alcohol, melted at 131° C. (Kofler) and had an elemental analysis, calculated for $C_{13}H_{15}N_4O_3Cl$, of:

| %          | C     | H    | N     | O     | Cl    |
| ---------- | ----- | ---- | ----- | ----- | ----- |
| Calculated:| 45.73 | 3.84 | 17.78 | 0.15  | 22.50 |
| Found:     | 45.61 | 3.88 | 17.69 | 10.26 | 22.43 |

2nd Stage:

Quaternization

The suspension of 4.7 g (0.015 mol) of (4,5-dichloro-2-nitrophenyl)(3-(imidazol-1-yl)propyl)amine obtained above in the preceding stage and 1.6 ml (0.017 mol) of dimethyl sulphate in 75 ml of ethyl acetate was prepared and was left for 2 hours at room temperature with stirring.

The crystallized precipitate was filtered off, washed several times in ethyl acetate, reslurried in the minimum amount of absolute ethanol and dried at 50° C. under vacuum.

4.5 g of yellow crystals were obtained, which crystals melted at 100° C. (Kofler) and had an elemental analysis, calculated for $C_{14}H_{18}N_4O_6SCl_2$, of:

| % | C | H | N | O | S | Cl |
|---|---|---|---|---|---|---|
| Calculated: | 38.11 | 4.11 | 12.70 | 21.75 | 7.27 | 16.07 |
| Found: | 38.14 | 4.16 | 12.89 | 21.89 | 7.17 | 15.80 |

Example 2

Preparation of the Compound of Formula $(I)_1$ 3-(3-(4-Chloro-5-methoxy-2-nitrophenylamino)propyl)-1-methyl-3H-imidazol-1-ium Methyl Sulphate 1st Stage:

Synthesis of (4-Chloro-5-methoxy-2-nitrophenyl)(3-(imidazol-1-yl)propyl)amine

A solution of 12.6 g (0.04 mol) of (4,5-dichloro-2-nitrophenyl)(3-(imidazol-1-yl)propyl)amine obtained in the first stage of Example 1 and 0.08 mol of sodium methoxide in 100 ml of methanol was heated with stirring for one hour at reflux.

The mixture was poured into 500 g of ice-cold water and the crystallized precipitate was filtered off, reslurried in water and dried under vacuum over phosphorus pentoxide.

9.5 g of yellow crystals were obtained, which crystals, after purification by recrystallization from refluxing ethanol, melted at 178° C. (Kofler) and had an elemental analysis, calculated for $C_{13}H_{15}N_4O_3Cl$, of:

| % | C | H | N | O | Cl |
|---|---|---|---|---|---|
| Calculated: | 50.25 | 4.87 | 18.03 | 15.45 | 11.41 |
| Found: | 49.79 | 4.98 | 17.44 | 16.36 | 11.23 |

2nd Stage:

Quaternization

The procedure described for Example 1 (2nd stage) was used.

From 4.7 g (0.015 mol) of (4-chloro-5-methoxy-2-nitrophenyl)(3-(imidazol-1-yl)propyl)amine obtained above in the preceding stage and from 1.6 ml (0.017 mol) of dimethyl sulphate in 75 ml of ethyl acetate, 5.7 g of yellow crystals were obtained, which crystals melted at 104° C. (Kofler) and had an elemental analysis, calculated for $C_{15}H_{21}N_4O_7SCl$, of:

| % | C | H | N | O | S | Cl |
|---|---|---|---|---|---|---|
| Calculated: | 41.24 | 4.85 | 12.82 | 25.64 | 7.34 | 8.12 |
| Found: | 41.16 | 4.84 | 12.86 | 25.44 | 7.18 | 7.94 |

Example 3

Preparation of the Compound of Formula $(I)_3$ 3-(3-(4-Chloro-5-methylsulphanyl-2-nitrophenylamino)propyl)-1-methyl-3H-imidazol-1-ium Methyl Sulphate 1st Stage:

Synthesis of (4-Chloro-5-methylsulphanyl-2-nitrophenyl)(3-(imidazol-1-yl)propyl)amine A solution of 12.6 g (0.04 mol) of (4,5-dichloro-2-nitrophenyl)(3-(imidazol-1-yl)propyl)amine obtained in the first stage of Example 1 and 4.0 g of sodium thiomethoxide in 70 ml of 1,2-dimethoxyethane was heated with stirring for one hour at reflux.

The mixture was poured into 500 g of ice-cold water and the crystallized precipitate was filtered off, reslurried in water and dried under vacuum over phosphorus pentoxide.

9.5 g of orange-yellow crystals were obtained, which crystals, after purification by recrystallization from refluxing 1,2-dimethoxyethane, melted at 152° C. (Kofler) and had an elemental analysis, calculated for $C_{13}H_{15}N_4O_2SCl$, of:

| % | C | H | N | O | S | Cl |
|---|---|---|---|---|---|---|
| Calculated: | 47.78 | 4.63 | 17.14 | 9.79 | 9.81 | 10.85 |
| Found: | 47.42 | 4.59 | 17.11 | 9.95 | 9.81 | 10.96 |

2nd Stage:

Quaternization

The procedure described for Example 1 (2nd stage) was used.

From 4.9 g (0.015 mol) of (4-chloro-5-methylsulphanyl-2-nitrophenyl)(3-(imidazol-1-yl)propyl)amine obtained above in the preceding stage and from 1.6 ml (0.017 mol) of dimethyl sulphate in 75 ml of ethyl acetate, 5.3 g of yellow crystals were obtained, which crystals melted at 102° C. (Kofler) and had an elemental analysis, calculated for $C_{12}H_{21}N_4O_6SCl$, of:

| % | C | H | N | O | S | Cl |
|---|---|---|---|---|---|---|
| Calculated: | 39.78 | 4.67 | 12.37 | 21.19 | 14.16 | 7.83 |
| Found: | 39.77 | 4.59 | 12.45 | 21.23 | 13.95 | 7.96 |

Example 4

Preparation of the Compound of Formula $(I)_5$ 1,3-Dimethyl-2-(3-methylamino-4-nitrophenylsulphanyl)-3H-imidazol-1-ium Methyl Sulphate 1st Stage:

Synthesis of Methyl(5-(1-methyl-1H-imidazol-2-ylsulphanyl)-2-nitrophenyl)amine

A mixture of 9.33 g (0.05 mol) of (5-chloro-2-nitrophenyl)methylamine (RN 35966-84-8), 8.0 g (0.07 mol) of 1-methyl-1H-imidazole-2-thiol (RN 60-56-0) and 10.4 g (0.075 mol) of potassium carbonate in 30 ml of N-methylpyrrolidone was heated for 4 hours at 120° C.

The mixture was poured into 250 g of ice-cold water and the crystallized precipitate was filtered off, reslurried in water and dried under vacuum over phosphorus pentoxide.

12 g of dark yellow crystals were obtained, which crystals, after purification by recrystallization from refluxing ethanol, melted at 140° C. (Kofler) and had an elemental analysis, calculated for $C_{11}H_{12}N_4O_2S$, of:

| % | C | H | N | O | S |
|---|---|---|---|---|---|
| Calculated: | 49.99 | 4.58 | 21.20 | 12.11 | 12.13 |
| Found: | 49.81 | 4.65 | 21.20 | 12.35 | 12.18 |

2nd Stage:

Quaternization

The procedure described for Example 1 (2nd stage) was used.

From 5.3 g (0.02 mol) of methyl(5-(1-methyl-1H-imidazol-2-ylsulphanyl)-2-nitrophenyl)amine obtained above in the preceding stage and from 2.09 ml (0.022 mol) of dimethyl sulphate in 100 ml of ethyl acetate, 6.0 g of orange-yellow crystals were obtained, which crystals melted at 170° C. (Kofler) and had an elemental analysis, calculated for $C_{13}H_{18}N_4O_6S$, of:

| % | C | H | N | O | S |
|---|---|---|---|---|---|
| Calculated: | 39.99 | 4.65 | 14.35 | 24.59 | 16.42 |
| Found: | 39.98 | 4.79 | 14.40 | 24.72 | 16.33 |

Example 5

Preparation of the Compound of Formula $(I)_6$ 1-{2-(5-(2-Hydroxyethylamino)-2-methyl-4-nitrophenoxy)ethyl}-3-methyl-3H-imidazol-1-ium Bromide 1st Stage:

Synthesis of the 2-Chloroethyl Ester of (5-Hydroxy-4-methyl-2-nitrophenyl)carbamic Acid The suspension of 19.7 g (0.118 mol) of 5-amino-2-methyl-4-nitrophenol (RN 37066-92-5) and 6.6 g (0.066 mol) of calcium carbonate in 60 ml of dioxane was heated with stirring on a refluxing water bath; 14.5 ml (0.14 mol) of 2-chloroethyl chloroformate (RN 627-11-2) were added over 5 minutes and heating was continued for 1½ h on the refluxing water bath.

The mixture was poured onto 500 g of ice-cold water and the crystallized precipitate was filtered off, reslurried in water and dried under vacuum over phosphorus pentoxide.

26.9 g of cream-colored crystals were obtained, which crystals, after purification by recrystallization from refluxing ethyl acetate, melted at 186° C. (Kofler) and had an elemental analysis, calculated for $C_{10}H_{11}N_2O_5Cl$, of:

| % | C | H | N | O | Cl |
|---|---|---|---|---|---|
| Calculated: | 43.73 | 4.04 | 10.20 | 29.12 | 12.91 |
| Found: | 43.77 | 4.04 | 10.17 | 28.92 | 12.87 |

2nd Stage:

Synthesis of 5-(2-Hydroxyethylamino)-2-methyl-4-nitrophenol

A mixture of 12.5 g (0.0455 mol) of 2-chloroethyl ester of (5-hydroxy-4-methyl-2-nitrophenyl)carbamic acid obtained above in the preceding stage and 36 ml of 5N sodium hydroxide solution was heated for ¾ of an hour on a refluxing water bath.

The mixture was cooled, 50 g of ice were added, the mixture was acidified with aqueous hydrochloric acid and the crystallized precipitate was filtered off, reslurried in water and dried at 55° C. under vacuum over phosphorus pentoxide.

9.5 g of red-brown crystals were obtained, which crystals, after purification by recrystallization from refluxing ethanol, melted at 204° C. (Kofler) and had an elemental analysis, calculated for $C_9H_{12}N_2O_4$, of:

| % | C | H | N | O |
|---|---|---|---|---|
| Calculated: | 50.94 | 5.70 | 13.20 | 30.16 |
| Found: | 50.96 | 5.74 | 13.40 | 30.08 |

3rd Stage:

Synthesis of 2-(5-(2-Bromoethoxy)-4-methyl-2-nitrophenylamino)ethanol

The suspension of 18.4 g (0.0867 mol) of 5-(2-hydroxyethylamino)-2-methyl-4-nitrophenol obtained above in the preceding stage and 6.2 g (0.104 mol) of calcium oxide in 80 ml of dimethylformamide was heated with stirring on a refluxing water bath; 22.5 ml (0.26 mol) of 1,2-dibromoethane (RN 106-93-4) were added and heating was continued for 4 h on the refluxing water bath.

The mixture was poured onto 150 g of ice-cold water and the crystallized precipitate was filtered off, reslurried in water and dried under vacuum at 45° C. over phosphorus pentoxide.

19.2 g of orange crystals were obtained, which crystals, after purification by medium-pressure chromatography on a column of silica gel (heptane and ethyl acetate gradient), melted at 124° C. (Kofler).

4th Stage:

Quaternization

The suspension of 5.5 g (0.0172 mol) of 2-(5-(2-bromoethoxy)-4-methyl-2-nitrophenylamino)ethanol obtained in the preceding stage and 3.4 g (0.04 mol) of 1-methyl-1H-imidazole (RN 616-47-7) in 20 ml of toluene was prepared.

The suspension was heated at reflux of the toluene with stirring for 4 hours, filtered off under refluxing conditions and reslurried twice in ethyl acetate and then in absolute ethanol.

After drying at 40° C. under vacuum, orange-yellow crystals (6.2 g) of 1-{2-(5-(2-hydroxyethylamino)-2-methyl-4-nitrophenoxy)ethyl}-3-methyl-3H-imidazol-1-ium bromide were obtained, which crystals melt at 156° C. (Kofler) and had an elemental analysis, calculated for $C_{15}H_{21}N_4O_4Br$, of:

| % | C | H | N | O | Br |
|---|---|---|---|---|---|
| Calculated: | 44.90 | 5.28 | 13.96 | 15.95 | 19.91 |
| Found: | 44.53 | 5.39 | 13.73 | 16.56 | 19.66 |

Example 6

Preparation of the Compound of Formula $(I)_4$ 3-(3-(4-methoxy-2-nitrophenylamino)propyl)-1-methyl-3H-imidazol-1-ium Methyl Sulphate Hydrate 1st Stage:

Synthesis of (3-(Imidazol-1-yl)propyl)(4-methoxy-2-nitropheny/)amine

A mixture of 18.7 g (0.1 mol) of 1-chloro-4-methoxy-2-nitrobenzene (RN 10298-80-3) and 84 ml of 3-(imidazol-1-yl)propylamine (RN 5036-48-6) was heated with stirring for 4 hours at 100–110° C.

The mixture was poured onto 400 g of ice-cold water; the oil which separated by settling was extracted with ethyl acetate; the ethyl acetate extract was dried over sodium sulphate, filtered and evaporated to dryness under reduced pressure.

An orange oil (22.7 g) was obtained, which oil crystallized (melting at 95° C., Kofler) after purification by chromatography on a column of silica gel (heptane and ethyl acetate gradient) and had an elemental analysis, calculated for $C_{13}H_{16}N_4O_3$, of:

| %          | C     | H    | N     | O     |
|------------|-------|------|-------|-------|
| Calculated: | 56.51 | 5.84 | 20.28 | 17.37 |
| Found:      | 56.25 | 5.86 | 20.48 | 17.28 |

2nd Stage:
Quaternization

The suspension of 5.5 g (0.02 mol) of (3-(imidazol-1-yl)propyl)(4-methoxy-2-nitrophenyl)amine obtained above in the preceding stage and 2.09 ml (0.022 mol) of dimethyl sulphate in 100 ml of ethyl acetate was prepared and was left for 3 hours at room temperature with stirring.

The oil which separated by settling was washed several times in ethyl acetate and dried at 50° C. under vacuum.

7.7 g of orange oil were obtained, the elemental analysis of which, calculated for $C_{15}H_{22}N_4O_7S+H_2O$, was:

| %          | C     | H    | N     | O     | S    |
|------------|-------|------|-------|-------|------|
| Calculated: | 42.85 | 5.75 | 13.33 | 30.44 | 7.63 |
| Found:      | 42.54 | 5.84 | 13.32 | 29.78 | 8.43 |

Example 7

Preparation of the Compound of Formula $(I)_7$ 3-{3-(4-(2-Hydroxyethoxy)-2-nitrophenylamino)propyl}-1-methyl-3H-imidazol-1-ium Methyl Sulphate 1st Stage:
Synthesis of 2-(4-(3-(Imidazol-1-yl)propylamino)-3-nitrophenoxy)ethanol The procedure described for Example 6 (1st stage) was used.

From 21.7 g (0.1 mol) of 2-(4-chloro-3-nitrophenoxy)ethanol (RN 59820-27-8) and from 84 ml of 3-(imidazol-1-yl)propylamine (RN 5036-48-6), 29.0 g of orange crystals were obtained, which crystals, after purification by medium-pressure chromatography on a column of silica gel (heptane and ethyl acetate gradient), melted at 60° C. (Kofler).

2nd Stage:
Quaternization

The procedure described for Example 6 (2nd stage) was used.

From 4.5 g (0.0147 mol) of 2-(4-(3-(imidazol-1-yl)propylamino)-3-nitrophenoxy)ethanol obtained above in the preceding stage and from 1.54 ml (0.016 mol) of dimethyl sulphate in 75 ml of ethyl acetate, 3.3 g of orange crystals were obtained, which crystals melt at 133° C. (Kofler) and had an elemental analysis, calculated for $C_{16}H_{24}N_4O_8S$, of:

| %          | C     | H    | N     | O     | S    |
|------------|-------|------|-------|-------|------|
| Calculated: | 44.44 | 5.59 | 12.96 | 29.60 | 7.41 |
| Found:      | 44.38 | 5.55 | 12.92 | 29.77 | 7.32 |

Example 8

Preparation of the Compound of Formula $(I)_8$ 3-Methyl-1-(2-(4-nitrophenylamino)ethyl)-3H-imidazol-1-ium Bromide The procedure described for Example 5 (4th stage) was used.

From 49.0 g (0.2 mol) of (2-bromoethyl)(4-nitrophenyl)amine (RN 55851-35-9) and from 19.8 g (0.24 mol) of 1-methyl-1H-imidazole (RN 616-47-7) in 200 ml of toluene, pale yellow crystals (62.3 g) of 3-methyl-1-(2-(4-nitrophenylamino)ethyl)-3H-imidazol-1-ium bromide were obtained, which crystals melt at 214° C. (Kofler) and had an elemental analysis, calculated for $C_{12}H_{15}N_4O_2Br$, of:

| %          | C     | H    | N     | O    | Br    |
|------------|-------|------|-------|------|-------|
| Calculated: | 44.05 | 4.62 | 17.12 | 9.78 | 24.42 |
| Found:      | 44.14 | 4.57 | 17.03 | 9.78 | 24.37 |

Example 9

Preparation of the Compound of Formula $(I)_9$ 1-Methyl-3-(3-(4-nitrophenylamino)propyl)-3H-imidazol-1-ium Methyl Sulphate 1st Stage:
Synthesis of (3-(Imidazol-1-yl)propyl)(4-nitrophenyl)amine The procedure described for Example 1 (1st stage) was used.

From 28.2 g (0.2 mol) of 1-fluoro-4-nitrobenzene (RN 350-46-9) and from 31.3 g (0.25 mol) of 3-(imidazol-1-yl)propylamine (RN 5036-48-6), yellow crystals (36.3 g) were obtained in ½ an hour, which crystals melted at 124° C. after purification by recrystallization from refluxing ethanol and had an elemental analysis, calculated for $C_{12}H_{14}N_4O_2$, of:

| %          | C     | H    | N     | O     |
|------------|-------|------|-------|-------|
| Calculated: | 58.53 | 5.73 | 22.75 | 12.99 |
| Found:      | 58.17 | 5.75 | 22.67 | 13.45 |

2nd Stage:
Quaternization

The procedure described for Example 1 (2nd stage) was used.

From 30.4 g (0.123 mol) of (3-(imidazol-1-yl)propyl)(4-nitrophenyl)amine obtained above in the preceding stage and from 12.9 ml (0.135 mol) of dimethyl sulphate in 600 ml of ethyl acetate, 37.6 g of yellow crystals were obtained, which crystals melted at 74° C. (Kofler) and had an elemental analysis, calculated for $C_{14}H_{20}N_4O_6S$, of:

| %          | C     | H    | N     | O     | S    |
|------------|-------|------|-------|-------|------|
| Calculated: | 45.15 | 5.41 | 15.04 | 25.78 | 8.61 |
| Found:      | 44.85 | 5.50 | 14.91 | 25.97 | 8.49 |

Example 10

Preparation of the Compound of Formula $(I)_{10}$ 1-(3-(2-Amino-5-nitrophenoxy)propyl)-3-methyl-3H-imidazol-1-ium Chloride Hydrochloride 1st Stage:
Synthesis of N-(2-(3-Chloropropoxy)-4-nitrophenyl)acetamide A mixture of 98.1 g (0.5 mol) of N-(2-hydroxy4-nitrophenyl)acetamide (RN 121-88-0) and 69.2 g (0.5 mol) of potassium carbonate in 500 ml of dimethylformamide was heated with stirring at 50° C.; 113.0 g (1 mol) of 1,3-dichloropropane (RN 142-28-9) were then added and heating was continued at 50° C. for one hour.

The mixture was poured into 4 liters of ice-cold water and the crystallized precipitate was filtered off, reslurried in water and then in isopropyl alcohol and dried under vacuum in 40° C. over phosphorus pentoxide. 113.5 g of beige crystals were obtained, which crystals, after purification by recrystallization from refluxing isopropyl acetate, melted at 121° C.

The elemental analysis, calculated for $C_{11}H_{13}N_2O_4Cl$, was:

| % | C | H | N | O | Cl |
|---|---|---|---|---|---|
| Calculated: | 48.95 | 4.81 | 10.27 | 23.47 | 13.00 |
| Found: | 48.33 | 4.84 | 10.14 | 22.67 | 12.87 |

2nd Stage:

Synthesis of 1-(3-(2-Acetylamino-5-nitrophenoxy)propyl)-3-methyl-3H-imidazol-1-ium Chloride The procedure described for Example 5 (4th stage) was used.

From 27.2 g (0.1 mol) of N-(2-(3-chloropropoxy)-4-nitrophenyl)acetamide obtained above in the preceding stage and from 9.9 g (0.12 mol) of 1-methyl-1H-imidazole (RN 616-47-7) in 120 ml of toluene, pale yellow crystals (21.5 g) of 1-(3-(2-acetylamino-5-nitrophenoxy)propyl)-3-methyl-3H-imidazol-1-ium chloride were obtained, which crystals melted at 227° C. (Kofler) and had an elemental analysis, calculated for $C_{15}H_{19}N_4O_4Cl$, of:

| % | C | H | N | O | Cl |
|---|---|---|---|---|---|
| Calculated: | 50.78 | 5.40 | 15.79 | 18.04 | 9.99 |
| Found: | 50.69 | 5.36 | 15.74 | 18.23 | 9.79 |

3rd Stage:

Deacetylation 14.0 g (0.039 mol) of 1-(3-(2-acetylamino-5-nitrophenoxy)propyl)-3-methyl-3H-imidazol-1-ium chloride obtained above in the preceding stage in 50 ml of a solution (5N) of hydrochloric acid in absolute ethanol were heated for one hour at reflux of the ethyl alcohol.

The mixture was cooled in an ice bath and the crystallized precipitate was filtered off, reslurried in absolute ethanol and dried at 50° C. under vacuum over potassium hydroxide.

Pale yellow crystals (10.0 g) of 1-(3-(2-amino-5-nitrophenoxy)propyl)-3-methyl-3H-imidazol-1-ium chloride hydrochloride were obtained, which crystals melt at 206° C. (Kofler) and had an elemental analysis, calculated for $C_{13}H_{18}N_4O_3Cl_2$, of:

| % | C | H | N | O | Cl |
|---|---|---|---|---|---|
| Calculated: | 44.71 | 5.20 | 16.04 | 13.74 | 20.30 |
| Found: | 44.43 | 5.20 | 15.78 | 13.52 | 19.90 |

Example 11

Preparation of the Compound of Formula $(I)_{11}$ 3-(3-(4,5-Dichloro-2-nitrophenylamino)propyl)-1-(3-(trimethylsilanyl)propyl)-3H-imidazol-1-ium Chloride Hydrate 1st Stage:

Quaternization

A solution of 15.76 g (0.05 mol) of (4,5-dichloro-2-nitrophenyl)(3-(imidazol-1-yl)propyl)amine obtained in the first stage of Example 1 and 9.0 g (0.06 mol) of 3-chloropropyltrimethylsilane (RN 2344-83-4) in 50 ml of 2-methyl-1-propanol was heated with stirring at reflux for 23 hours.

The orange oil obtained after evaporting the reaction mixture to dryness was dried at 45° C. under vacuum over phosphorus pentoxide and then it was taken up in 50 ml of ethyl acetate.

The expected compound crystallized; after filtering off, washing with ethyl acetate and drying, 12.2 g of orange-yellow crystals were obtained, which crystals melt at 122–124° C. (Kofler) and had an elemental analysis, calculated for $C_{18}H_{27}N_4O_2Cl_3Si.H_2O$, of:

| % | C | H | N | Cl |
|---|---|---|---|---|
| Calculated: | 44.68 | 6.04 | 11.58 | 21.98 |
| Found: | 44.98 | 5.95 | 11.67 | 21.93 |

EXAMPLES OF DYEING COMPOSITIONS

Example 1

The following dyeing composition was prepared:

(all contents expressed in grams—A.M. denotes Active Material)

Dye of formula $(I)_{11}$ . . . 0.484

Hydroxyethylcellulose, sold under the name

NATROSOL 250 MR by the company Aqualon . . . 0.72

Benzyl alcohol . . . 4

Polyethylene glycol with 6 ethylene oxide units . . . 6

($C_8$–$C_{10}$)Alkyl polyglucoside as an aqueous solution comprising 60% of A.M., sold under the name ORAMIX CG 110 by the company Seppic . . . 4.5 A.M.

Phosphate buffer, pH 7 . . . q.s. for . . . 100

The above composition was applied to locks of natural or permed grey hair comprising 90% white hairs and was left to stand for 20 minutes. After rinsing with ordinary water and drying, the hair was dyed in an intense yellow shade.

Examples 2 to 7

The six following dyeing compositions were prepared:

(all contents expressed in grams)

| EXAMPLE | 2 | 3 | 4 | 5 | 6 | 7 |
|---|---|---|---|---|---|---|
| Compound of formula (I)$_1$ | 0.437 | | | | | |
| Compound of formula (I)$_2$ | | 0.441 | | | | |
| Compound of formula (I)$_6$ | | | 0.401 | | | |
| Compound of formula (I)$_3$ | | | | 0.453 | | |
| Compound of formula (I)$_7$ | | | | | 0.432 | |
| Compound of formula (I)$_4$ | | | | | | 0.402 |
| Ethylene glycol monoethyl ether | 10 | 10 | 10 | 10 | 10 | 10 |
| Cetyl/stearyl alcohol/ sodium lauryl sulphate mixture, sold under the name SINNOWAX SX by the company Henkel | 2 | 2 | 2 | 2 | 2 | 2 |
| Oxyethylenated (3 EO) linear fatty alcohol ($C_{13}$–$C_{15}$), sold under the name SYNPERONIC A3 by the company I. C. I. | 3 | 3 | 3 | 3 | 3 | 3 |
| Oxyethylenated (7 EO) linear fatty alcohol ($C_{13}$–$C_{15}$), sold under the name SYNPERONIC A7 by the company I. C. I. | 2 | 2 | 2 | 2 | 2 | 2 |
| Trimethylcetylammonium bromide | 1.5 | 1.5 | 1.5 | 1.5 | 1.5 | 1.5 |
| Monoethanolamine q.s. pH | 8 | 8 | 8 | 8 | 8 | 8 |
| Demineralized water q.s. for | 100 | 100 | 100 | 100 | 100 | 100 |

Each of the above compositions was applied to locks of natural grey hair comprising 90% white hairs and was left to stand for 20 minutes. After rinsing with ordinary water and drying, the hair was dyed in a shade which is expressed in the table below.

| | |
|---|---|
| Composition of Example 2 | yellow |
| Composition of Example 3 | yellow |
| Composition of Example 4 | yellow |
| Composition of Example 5 | yellow |
| Composition of Example 6 | coppery golden |
| Composition of Example 7 | coppery golden |

What is claimed is:

1. A dyeing composition for keratinous substances comprising, in a medium appropriate for dyeing, at least one cationic monobenzene nitroaniline of the following formula (I) or an acid addition salt thereof, said at least one cationic monobenzene nitroaniline being present in said composition in an amount effective for direct dyeing of keratinous fibers:

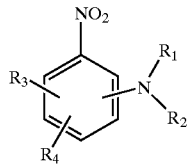

(I)

wherein:

$R_1$ and $R_2$, which can be identical or different, are chosen from a hydrogen atom; a Z group as defined below; a ($C_1$–$C_6$)alkyl radical; a monohydroxy($C_1$–$C_6$)alkyl radical; a polyhydroxy($C_2$–$C_6$)alkyl radical; a ($C_1$–$C_6$) alkoxy($C_1$–$C_6$)alkyl radical; an aryl radical; a benzyl radical; a cyano($C_1$–$C_6$)alkyl radical; a carbamyl ($C_1$–$C_6$)alkyl radical; an N-($C_1$–$C_6$)alkylcarbamyl ($C_1$–$C_6$)alkyl radical; an N,N-di($C_1$–$C_6$)alkylcarbamyl ($C_1$–$C_6$)alkyl radical; a thiocarbamyl($C_1$–$C_6$)alkyl radical; a trifluoro($C_1$–$C_6$)alkyl radical; a sulpho ($C_1$–$C_6$)alkyl radical; a ($C_1$–$C_6$)alkylcarboxy($C_1$–$C_6$) alkyl radical; a ($C_1$–$C_6$)alkylsulphinyl($C_1$–$C_6$)alkyl radical; an aminosulphonyl($C_1$–$C_6$)alkyl radical; an N—Z-aminosulphonyl($C_1$–$C_6$)alkyl radical; an N-($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylcarbonyl($C_1$–$C_6$)alkyl radical; an amino($C_1$–$C_6$)alkyl radical, wherein the alkyl is unsubstituted or substituted by one or more hydroxyl radicals; and an amino($C_1$–$C_6$)alkyl radical, wherein the alkyl is unsubstituted or substituted by one or more hydroxyl radicals and the amine is substituted by one or two identical or different radicals which may together form, with the nitrogen atom to which they are attached, a carbonaceous 5- or 6-membered ring or a 5- or 6-membered ring comprising one or more heteroatoms, or which are chosen from alkyl, monohydroxy($C_1$–$C_6$)alkyl, polyhydroxy($C_2$–$C_6$)alkyl, ($C_1$–$C_6$)alkylcarbonyl, carbamyl, N-($C_1$–$C_6$) alkylcarbamyl, N,N-di($C_1$–$C_6$)alkylcarbamyl, ($C_1$–$C_6$) alkylsulphonyl, formyl, trifluoro($C_1$–$C_6$)alkylcarbonyl, ($C_1$–$C_6$)alkylcarboxyl and thiocarbamyl radicals, and from a Z group as defined below;

$R_3$ and $R_4$, which can be identical or different, are chosen from a hydrogen atom; a halogen atom; a Z group as defined below; a ($C_1$–$C_6$)alkylcarbonyl radical; an amino($C_1$–$C_6$)alkylcarbonyl radical; an N—Z-amino ($C_1$–$C_6$)alkylcarbonyl radical; an N-($C_1$–$C_6$) alkylamino($C_1$–$C_6$)alkylcarbonyl radical; an N,N-di ($C_1$–$C_6$)alkylamino($C_1$–$C_6$)alkylcarbonyl radical; an amino($C_1$–$C_6$)alkylcarbonyl($C_1$–$C_6$)alkyl radical; an N—Z-amino($C_1$–$C_6$)alkylcarbonyl($C_1$–$C_6$)alkyl radical; an N-($C_1$–$C_6$)alkylamino($C_1$–$C_6$)alkylcarbonyl ($C_1$–$C_6$)alkyl radical; an N,N-di($C_1$–$C_6$)alkylamino- ($C_1$–$C_6$)alkylcarbonyl($C_1$–$C_6$)alkyl radical; a carboxyl radical; a ($C_1$–$C_6$)alkylcarboxyl radical; a ($C_1$–$C_6$) alkylsulphonyl radical; an aminosulphonyl radical; an N—Z-aminosulphonyl radical; an N-($C_1$–$C_6$) alkylaminosulphonyl radical; an N,N-di($C_1$–$C_6$) alkylaminosulphonyl radical; an aminosulphonyl ($C_1$–$C_6$)alkyl radical; an N—Z-aminosulphonyl ($C_1$–$C_6$)alkyl radical; an N-($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a carbamyl radical; an N-(C₁–C₆)alkylcarbamyl radical; an N,N-di(C₁–C₆)alkylcarbamyl radical; a carbamyl (C₁–C₆)alkyl radical; an N-(C₁–C₆)alkylcarbamyl (C₁–C₆)alkyl radical; an N,N-di(C₁–C₆)alkylcarbamyl (C₁–C₆)alkyl radical; a (C₁–C₆)alkyl radical; a monohydroxy(C₁–C₆)alkyl radical; a polyhydroxy (C₂–C₆)alkyl radical; a (C₁–C₆)alkoxy(C₁–C₆)alkyl radical; a trifluoro(C₁–C₆)alkyl radical; a cyano radical; an OR₅ or —SR₅ group wherein R₅ is as defined below; and an amino(C₁–C₆)alkyl radical, wherein the alkyl is unsubstituted or substituted by one or more hydroxyl radicals, and the amine is unsubstituted or substituted by one or two identical or different radicals which may together form, with the nitrogen atom to which they are attached, a carbonaceous 5- or 6-membered ring or a 5- or 6-membered ring comprising one or more heteroatoms, or which are chosen from (C₁–C₆)alkyl, monohydroxy(C₁–C₆)alkyl, polyhydroxy(C₂–C₆)alkyl, (C₁–C₆)alkylcarbonyl, carbamyl, N-(C₁–C₆)alkylcarbamyl, N,N-di(C₁–C₆)alkylcarbamyl, (C₁–C₆)alkylsulphonyl, formyl, trifluoro(C₁–C₆)alkylcarbonyl, (C₁–C₆)alkylcarboxyl and thiocarbamyl radicals, and from a Z group as defined below;

R₅ is chosen from a hydrogen atom; a (C₁–C₆)alkyl radical; a monohydroxy(C₁–C₆)alkyl radical; a polyhydroxy(C₂–C₆)alkyl radical; a Z group as defined below; a (C₁–C₆)alkoxy(C₁–C₆)alkyl radical; an aryl radical; a benzyl radical; a carboxy(C₁–C₆)alkyl radical; a (C₁–C₆)alkylcarboxy(C₁–C₆)alkyl radical; a cyano(C₁–C₆)alkyl radical; a carbamyl(C₁–C₆)alkyl radical; an N-(C₁–C₆)alkylcarbamyl(C₁–C₆)alkyl radical; an N,N-di(C₁–C₆)alkylcarbamyl(C₁–C₆)alkyl radical; a trifluoro(C₁–C₆)alkyl radical; an aminosulphonyl (C₁–C₆)alkyl radical; an N—Z-aminosulphonyl (C₁–C₆)alkyl radical; an N-(C₁–C₆)alkylaminosulphonyl(C₁–C₆)alkyl radical; an N,N-di(C₁–C₆)alkylaminosulphonyl(C₁–C₆)alkyl radical; a (C₁–C₆)alkylsulphinyl(C₁–C₆)alkyl radical; a (C₁–C₆)alkylsulphonyl(C₁–C₆)alkyl radical; a (C₁–C₆)alkylcarbonyl(C₁–C₆)alkyl radical; an amino(C₁–C₆)alkyl radical, wherein the alkyl is unsubstituted or substituted by one or more hydroxyl radicals; and an amino(C₁–C₆)alkyl radical, wherein the alkyl is unsubstituted or substituted by one or more hydroxyl radicals and the amine is substituted by one or two identical or different radicals which may together form, with the nitrogen atom to which they are attached, a carbonaceous 5- or 6-membered ring or a 5- or 6-membered ring comprising one or more heteroatoms, or which are chosen from (C₁–C₆)alkyl, monohydroxy(C₁–C₆)alkyl, polyhydroxy(C₂–C₆)alkyl, (C₁–C₆)alkylcarbonyl, formyl, trifluoro(C₁–C₆)alkylcarbonyl, (C₁–C₆)alkylcarboxyl, carbamyl, N-(C₁–C₆)alkylcarbamyl, N,N-di(C₁–C₆)alkylcarbamyl, thiocarbamyl and (C₁–C₆)alkylsulphonyl radicals, and from a Z group as defined below;

Z is chosen from the unsaturated cationic groups of following formulae (II) and (III) and the saturated cationic groups of following formula (IV):

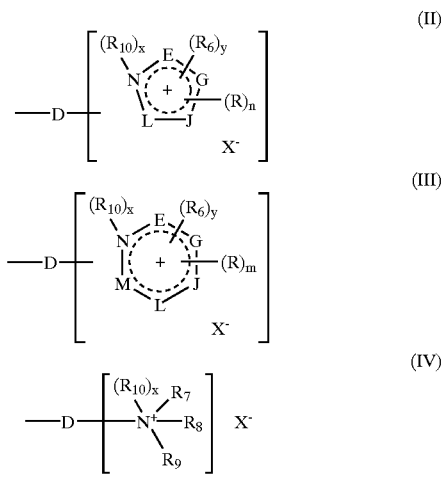

wherein:
D is a linking arm which is a linear or branched alkyl chain, which can be interrupted by one or more heteroatoms, can be substituted by one or more hydroxyl or (C₁–C₆)alkoxy radicals, and can carry one or more ketone functional groups;
the E, G, J, L and M vertices, which are identical or different, are chosen from carbon, oxygen, sulphur and nitrogen atoms;
n is an integer ranging from 0 to 4;
m is an integer ranging from 0 to 5;
the R radicals, which are identical or different, are chosen from a second Z group identical to or different from the first Z group; a halogen atom; a hydroxyl radical; a (C₁–C₆)alkyl radical; a monohydroxy(C₁–C₆)alkyl radical; a polyhydroxy (C₂–C₆)alkyl radical; a nitro radical; a cyano radical; a cyano(C₁–C₆)alkyl radical; a(C₁–C₆)alkoxy radical; a tri(C₁–C₆)alkylsilyl(C₁–C₆)alkyl radical; an amido radical; a formyl radical; a carboxyl radical; a (C₁–C₆)alkylcarbonyl radical; a thio radical; a thio (C₁–C₆)alkyl radical; a(C₁–C₆)alkylthio radical; an amino radical; an amino radical protected by a (C₁–C₆)alkylcarbonyl, carbamyl or (C₁–C₆)alkylsulphonyl radical; and an NHR" or NR"R'" group, wherein R" and R'", which are identical or different, are chosen from a (C₁–C₆)alkyl radical, a monohydroxy(C₁–C₆)alkyl radical and a polyhydroxy(C₂–C₆)alkyl radical;
R₆ is chosen from a (C₁–C₆)alkyl radical; a monohydroxy(C₁–C₆)alkyl radical; a polyhydroxy (C₂–C₆)alkyl radical;,a cyano(C₁–C₆)alkyl radical; a tri(C₁–C₆)alkylsilyl(C₁–C₆)alkyl radical; a (C₁–C₆)alkoxy(C₁–C₆)alkyl radical; a carbamyl(C₁–C₆)alkyl radical; a (C₁–C₆)alkylcarboxy(C₁–C₆)alkyl radical; a benzyl radical; and a second Z group identical to or different from the first Z group;
R₇, R₈ and R₉, which are identical or different, are chosen from a (C₁–C₆)alkyl radical; a monohydroxy (C₁–C₆)alkyl radical; a polyhydroxy(C₂–C₆)alkyl radical; a(C₁–C₆)alkoxy(C₁–C₆)alkyl radical; a cyano(C₁–C₆)alkyl radical; an aryl radical; a benzyl radical; an amido(C₁–C₆)alkyl radical; a tri(C₁–C₆)alkylsilyl(C₁–C₆)alkyl radical; and an amino(C₁–C₆)alkyl radical, wherein the amine is protected by a (C₁–C₆)alkylcarbonyl, carbamyl or (C₁–C₆)alkylsulphonyl radical; or wherein two of the R₇, R₈ and $R_9$ radicals together form, with the nitrogen atom to which they are attached, a saturated carbonaceous 5- or 6-membered ring or a saturated 5- or 6-membered ring which can comprise one or more heteroatoms, and which can be unsubstituted or substituted by a halogen atom, a hydroxyl radical, a $(C_1–C_6)$alkyl radical, a monohydroxy$(C_1–C_6)$alkyl radical, a polyhydroxy$(C_2–C_6)$alkyl radical, a nitro radical, a cyano radical, a cyano$(C_1–C_6)$alkyl radical, a $(C_1–C_6)$alkoxy radical, a tri$(C_1–C_6)$alkylsilyl$(C_1–C_6)$alkyl radical, an amido radical, a formyl radical, a carboxyl radical, a keto$(C_1–C_6)$alkyl radical, a thio radical, a thio$(C_1–C_6)$alkyl radical, a $(C_1–C_6)$alkylthio radical, an amino radical or an amino radical protected by a $(C_1–C_6)$alkylcarbonyl, carbamyl or $(C_1–C_6)$alkylsulphonyl radical; or wherein one of the $R_7$, $R_8$ and $R_9$ radicals is a second Z group identical to or different from the first Z group;

$R_{10}$ is chosen from a $(C_1–C_6)$alkyl radical; a monohydroxy$(C_1–C_6)$alkyl radical; a polyhydroxy $(C_2–C_6)$alkyl radical; an aryl radical; a benzyl radical; an amino$(C_1–C_6)$alkyl radical; an amino$(C_1–C_6)$ alkyl radical, wherein the amine is protected by a $(C_1–C_6)$alkylcarbonyl, carbamyl or $(C_1–C_6)$ alkylsulphonyl radical; a carboxy$(C_1–C_6)$alkyl radical; a cyano$(C_1–C_6)$alkyl radical; a carbamyl$(C_1–C_6)$ alkyl radical; a trifluoro$(C_1–C_6)$alkyl radical; a tri$(C_1–C_6)$alkylsilyl$(C_1–C_6)$alkyl radical; a sulphonamido$(C_1–C_6)$alkyl radical; a$(C_1–C_6)$ alkylcarboxy$(C_1–C_6)$alkyl radical; a $(C_1–C_6)$ alkylsulphinyl$(C_1–C_6)$alkyl radical; a $(C_1–C_6)$ alkylsulphonyl$(C_1–C_6)$alkyl radical; a $(C_1–C_6)$ alkylketo$(C_1–C_6)$alkyl radical; an N-$(C_1–C_6)$ alkylcarbamyl$(C_1–C_6)$alkyl radical; and an N-$(C_1–C_6)$alkylsulphonamido$(C_1–C_6)$alkyl radical;

x and y are integers equal to 0 or 1, with the provisos that:
in the unsaturated cationic groups of formula (II):
when x=0, the D linking arm is attached to the nitrogen atom,
when x=1, the D linking arm is attached to one of the E, G, J or L vertices,
y can take the value 1 only when:
1) the E, G, J and L vertices simultaneously represent a carbon atom and when the $R_6$ radical is carried by the nitrogen atom of the unsaturated ring; or
2) at least one of the E, G, J and L vertices represents a nitrogen atom to which the $R_6$ radical is attached;
in the unsaturated cationic groups of formula (III):
when x=0, the D linking arm is attached to the nitrogen atom,
when x=1, the D linking arm is attached to one of the E, G, J, L or M vertices,
y can take the value 1 only when at least one of the E, G, J, L and M vertices represents a divalent atom and when the $R_6$ radical is carried by the nitrogen atom of the unsaturated ring;
in the cationic groups of formula (IV):
when x=0, the D linking arm is attached to the nitrogen atom carrying the $R_7$, $R_8$ and $R_9$ radicals,
when x=1, two of the $R_7$, $R_8$ and $R_9$ radicals jointly form, with the nitrogen atom to which they are attached, a saturated carbonaceous 5- or 6-membered ring or a saturated 5- or 6-membered ring which can comprise one or more heteroatoms, and which can be unsubstituted or substituted by a halogen atom, a hydroxyl radical, a $(C_1–C_6)$alkyl radical, a monohydroxy$(C_1–C_6)$alkyl radical, a polyhydroxy$(C_2–C_6)$alkyl radical, a nitro radical, a cyano radical, a cyano$(C_1–C_6)$alkyl radical, $(C_1–C_6)$alkoxy radical, a tri$(C_1–C_6)$alkylsilyl $(C_1–C_6)$alkyl radical, an amido radical, a formyl radical, a carboxyl radical, a keto$(C_1–C_6)$alkyl radical, a thio radical, a thio$(C_1–C_6)$alkyl radical, a $(C_1–C_6)$alkylthio radical, an amino radical or an amino radical protected by a $(C_1–C_6)$ alkylcarbonyl, carbamyl or $(C_1–C_6)$ alkylsulphonyl radical; and the D linking arm is carried by a carbon atom of the said saturated ring;

$X^−$ represents a monovalent or divalent anion;
provided that:
at least one of $R_1$, $R_2$, $R_3$ and $R_4$ comprises at least one Z group of the formula (II), wherein at least one of the E, G, J, and L vertices represents a nitrogen atom; and
when one and only one of the $R_1$ or $R_2$ or $R_5$ radicals is a Z group wherein the D linking arm represents an alkyl chain comprising a ketone functional group, then said ketone functional group is not directly attached to the nitrogen atom of the $NR_1R_2$ group or to the oxygen atom of the $OR_5$ group when $R_1$ or $R_2$ is $OR_5$.

2. A composition according to claim 1, wherein D is a linear or branched alkyl chain comprising from 1 to 14 carbon atoms.

3. A composition according to claim 1, wherein D is a linear or branched alkyl chain interrupted by one or more heteroatoms chosen from oxygen, sulphur and nitrogen atoms.

4. A composition according to claim 1, wherein the rings of the Z unsaturated groups of formula (II) are chosen from pyrrole, imidazole, pyrazole, oxazole, thiazole and triazole rings.

5. A composition according to claim 1, wherein the rings of the Z unsaturated groups of formula (III) are chosen from pyridine, pyrimidine, pyrazine, oxazine and triazine rings.

6. A composition according to claim 1, wherein two of the $R_7$, $R_8$, and $R_9$ radicals in formula (IV) together form, with the nitrogen atom to which they are attached, a pyrrolidine ring, a piperidine ring, a piperazine ring or a morpholine ring, wherein said ring is unsubstituted or substituted by a halogen atom, a hydroxyl radical, a $(C_1–C_6)$alkyl radical, a monohydroxy$(C_1–C_6)$alkyl radical, a polyhydroxy$(C_2–C_6)$ alkyl radical, a nitro radical, a cyano radical, a cyano$(C_1–C_6)$ alkyl radical, a $(C_1–C_6)$alkoxy radical, a tri$(C_1–C_6)$alkylsilyl $(C_1–C_6)$alkyl radical, an amido radical, a formyl radical, a carboxyl radical, a $(C_1–C_6)$alkylcarbonyl radical, a thio radical, a thio$(C_1–C_6)$alkyl radical, a $(C_1–C_6)$alkylthio radical, an amino radical or an amino radical protected by a $(C_1–C_6)$alkylcarbonyl, carbamyl or $(C_1–C_6)$alkylsulphonyl radical.

7. A composition according to claim 1, wherein $X^−$ is chosen from a halogen atom, a hydroxide, a hydrogen sulphate and a $(C_1–C_6)$alkyl sulphate.

8. A composition according to claim 1, wherein said at least one cationic monobenzene nitroaniline is chosen from the following compounds:
3-(3-(4,5-dichloro-2-nitrophenylamino)propyl)-1-methyl-3H-imidazol-1-ium methyl sulphate,
3-(3-(4-chloro-5-methoxy-2-nitrophenylamino)propyl)-1-methyl-3H-imidazol-1-ium methyl sulphate,
3-(3-(4-chloro-5-methylsulphanyl-2-nitrophenylamino) propyl)-1-methyl-3H-imidazol-1-ium methyl sulphate, 1,3-dimethyl-2-(3-methylamino-4-nitrophenylsulphanyl)-3H-imidazol-1-ium methyl sulphate,
1-{-2-(5-(2-hydroxyethylamino)-2-methyl-4-nitrophenoxy)ethyl}-3-methyl-3H-imidazol-1-ium bromide,
3-(3-(4-methoxy-2-nitrophenylamino)propyl)-1-methyl-3H-imidazol-1-ium methyl sulphate hydrate,
3-{3-(4-(2-hydroxyethoxy)-2-nitrophenylamino)propyl}-1-methyl-3H-imidazol-1-ium methyl sulphate,
3-methyl-1-(2-(4-nitrophenylamino)ethyl)-3H-imidazol-1-ium bromide,
1-methyl-3-(3-(4-nitrophenylamino)propyl)-3H-imidazol-1-ium methyl sulphate,
1-(3-(2-amino-5-nitrophenoxy)propyl)-3-methyl-3H-imidazol-1-ium chloride hydrochloride,
3-(3-(4,5-dichloro-2-nitrophenylamino)propyl)-1-(3-(trimethylsilanyl)propyl)-3H-imidazol-1-ium chloride hydrate,
1-(3-(2-amino-5-nitrophenoxy)propyl)-2-methyl-2H-pyrazol-1-ium bromide,
1-methyl-3-(3-(2-nitrophenylamino)propyl)-3H-imidazol-1-ium methyl sulphate,
1-(3-chloropropyl)-3-(3-(4-nitrophenylamino)propyl)-3H-imidazol-1-ium chloride,
1-(2-hydroxyethyl)-3-(3-(4-nitrophenylamino)propyl)-3H-imidazol-1-ium chloride,
3-(3-(4-benzyloxy-2-nitrophenylamino)propyl)-1-methyl-3H-imidazol-1-ium methyl sulphate,
3-(3-(2-cyano-4-nitrophenylamino)propyl)-1-methyl-3H-imidazol-1-ium methyl sulphate,
1-methyl-3-(3-(2-methyl-4-nitrophenylamino)propyl)-3H-imidazol-1-ium methyl sulphate,
3-(3-(2-fluoro-4-nitrophenylamino)propyl)-1-methyl-3H-imidazol-1-ium methyl sulphate,
1-(2-(2-methoxy4-nitrophenylamino)ethyl)-3-methyl-3H-imidazol-1-ium bromide,
3-(3-(3-hydroxy-4-nitrophenylamino)propyl)-1-methyl-3H-imidazol-1-ium methyl sulphate,
3-(3-(2-chloro-4-nitrophenylamino)propyl)-1-methyl-3H-imidazol-1-ium methyl sulphate,
2-methyl-1-(2-(4-nitrophenylamino)ethyl)-2H-pyrazol-1-ium bromide,
1-(3-bromo-2-hydroxypropyl)-3-(3-(4-nitrophenylamino)propyl)-3H-imidazol-1-ium bromide,
1-(3-trimethylammonio-2-hydroxypropyl)-3-(3-(4-nitrophenylamino)propyl)-3H-imidazol-1-ium dichloride,
diethyl(2-hydroxyethyl)4-(4-nitrophenylamino)pentyl) ammonium chloride,
3-(3-(4-chloro-2-nitrophenylamino)propyl)-1-methyl-3H-imidazol-1-ium methyl sulphate,
3-(3-(2-chloro-6-nitrophenylamino)propyl)-1-methyl-3H-imidazol-1-ium methyl sulphate,
1-methyl-3-(2-(4-nitrophenylamino)butyl)-3H-imidazol-1-ium chloride,
3-methyl-1-(2-methyl-2-(4-nitrophenylamino)propyl)-3H-imidazol-1-ium chloride, and
1-{2-((2-(3-methyl-3H-imidazol-1-io)ethyl)(4-nitrophenyl)amino)ethyl}-3-methyl-3H-imidazol-1-ium dichloride.

9. A composition according to claim 8, wherein said at least one cationic monobenzene nitroaniline is chosen from the compounds of following formulae (I)$_1$ to (I)$_{11}$:

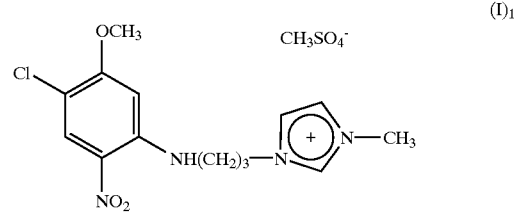

(I)$_1$

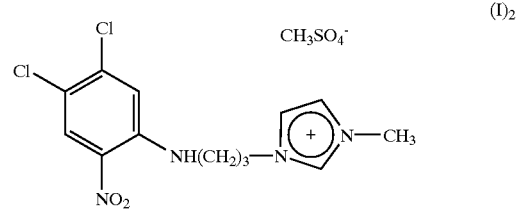

(I)$_2$

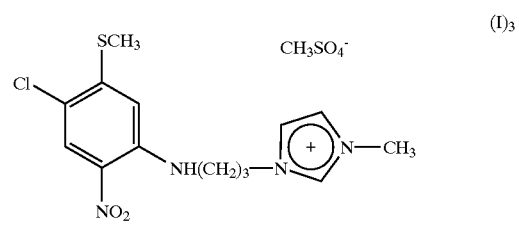

(I)$_3$

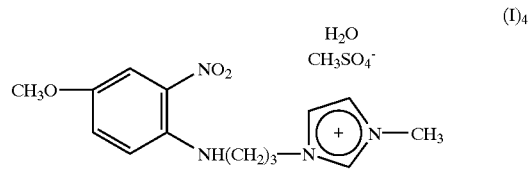

(I)$_4$

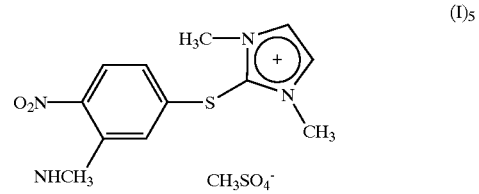

(I)$_5$

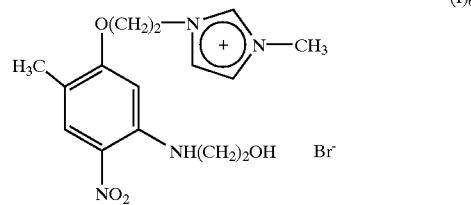

(I)$_6$

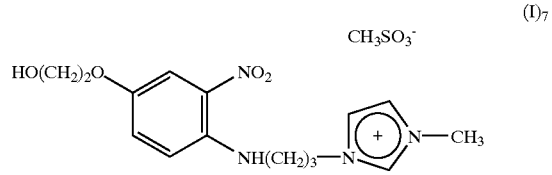

(I)$_7$

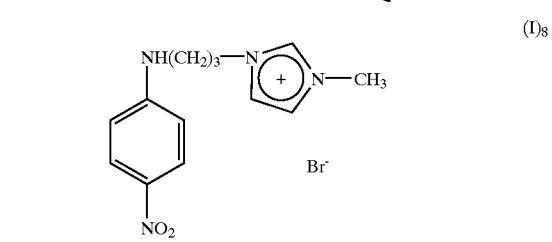

(I)$_8$

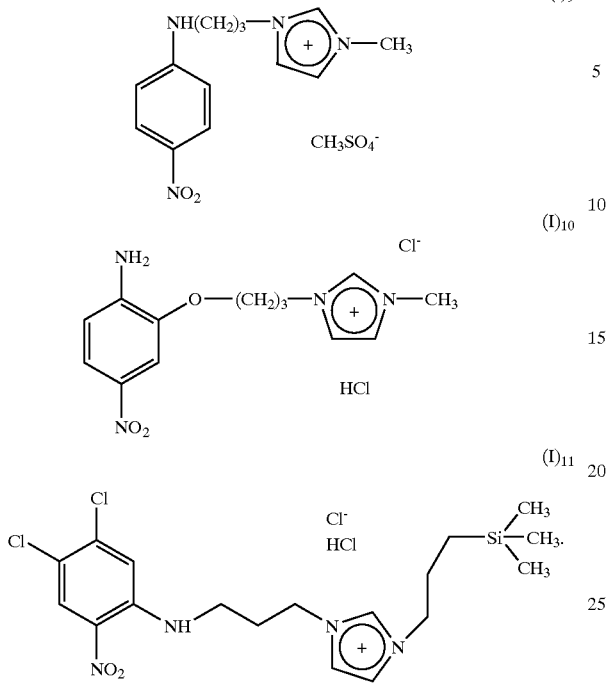

10. A composition according to claim 1, wherein said acid addition salts of said at least one cationic monobenzene nitroaniline of formula (I) are chosen from hydrochlorides, hydrobromides, sulphates, citrates, succinates, tartrates, lactates and acetates.

11. A composition according to claim 1, wherein said keratinous fibers are human keratinous fibers.

12. A composition according to claim 11, wherein said human keratinous fibers are hair.

13. A composition according to claim 1, wherein said composition has a pH ranging from 3 to 12.

14. A composition according to claim 1, wherein said at least one cationic monobenzene nitroaniline of formula (I) is present in an amount ranging from 0.005 to 12% by weight with respect to the total weight of the composition.

15. A composition according to claim 14, wherein said at least one cationic monobenzene nitroaniline of formula (I) is present in an amount ranging from 0.05 to 6% by weight with respect to the total weight of the composition.

16. A composition according to claim 1, wherein said medium appropriate for dyeing is an aqueous medium comprising water and/or organic solvents, said medium being present in said composition in an amount ranging from 1 to 40% by weight with respect to the total weight of the composition.

17. A process for dyeing keratinous fibers by direct coloring, comprising applying a dyeing composition to dry or wet keratinous fibers, said dyeing composition comprising, in a medium appropriate for dyeing, at least one cationic monobenzene nitroaniline of the following formula (I) or an acid addition salt thereof, said at least one cationic monobenzene nitroaniline being present in said composition in an amount effective for direct dyeing of keratinous fibers:

wherein:

$R_1$ and $R_2$, which can be identical or different, are chosen from a hydrogen atom; a Z group as defined below; a $(C_1-C_6)$alkyl radical; a monohydroxy$(C_1-C_6)$alkyl radical; a polyhydroxy$(C_2-C_6)$alkyl radical; a $(C_1-C_6)$alkoxy$(C_1-C_6)$alkyl radical; an aryl radical; a benzyl radical; a cyano$(C_1-C_6)$alkyl radical; a carbamyl$(C_1-C_6)$alkyl radical; an N-$(C_1-C_6)$alkylcarbamyl$(C_1-C_6)$alkyl radical; an N,N-di$(C_1-C_6)$alkylcarbamyl$(C_1-C_6)$alkyl radical; a thiocarbamyl$(C_1-C_6)$alkyl radical; a trifluoro$(C_1-C_6)$alkyl radical; a sulpho$(C_1-C_6)$alkyl radical; a $(C_1-C_6)$alkylcarboxy$(C_1-C_6)$alkyl radical; a $(C_1-C_6)$alkylsulphinyl$(C_1-C_6)$alkyl radical; an aminosulphonyl$(C_1-C_6)$alkyl radical; an N—Z-aminosulphonyl$(C_1-C_6)$alkyl radical; an N-$(C_1-C_6)$alkylaminosulphonyl$(C_1-C_6)$alkyl radical; an N,N-di$(C_1-C_6)$alkylaminosulphonyl$(C_1-C_6)$alkyl radical; a $(C_1-C_6)$alkylcarbonyl$(C_1-C_6)$alkyl radical; an amino$(C_1-C_6)$alkyl radical, wherein the alkyl is unsubstituted or substituted by one or more hydroxyl radicals; and an amino$(C_1-C_6)$alkyl radical, wherein the alkyl is unsubstituted or substituted by one or more hydroxyl radicals and the amine is substituted by one or two identical or different radicals which may together form, with the nitrogen atom to which they are attached, a carbonaceous 5- or 6-membered ring or a 5- or 6-membered ring comprising one or more heteroatoms, or which are chosen from alkyl, monohydroxy$(C_1-C_6)$alkyl, polyhydroxy$(C_2-C_6)$alkyl, $(C_1-C_6)$alkylcarbonyl, carbamyl, N-$(C_1-C_6)$alkylcarbamyl, N,N-di$(C_1-C_6)$alkylcarbamyl, $(C_1-C_6)$alkylsulphonyl, formyl, trifluoro$(C_1-C_6)$alkylcarbonyl, $(C_1-C_6)$alkylcarboxyl and thiocarbamyl radicals, and from a Z group as defined below;

$R_3$ and $R_4$, which can be identical or different, are chosen from a hydrogen atom; a halogen atom; a Z group as defined below; a $(C_1-C_6)$alkylcarbonyl radical; an amino$(C_1-C_6)$alkylcarbonyl radical; an N—Z-amino$(C_1-C_6)$alkylcarbonyl radical; an N-$(C_1-C_6)$alkylamino$(C_1-C_6)$alkylcarbonyl radical; an N,N-di$(C_1-C_6)$alkylamino$(C_1-C_6)$alkylcarbonyl radical; an amino$(C_1-C_6)$alkylcarbonyl$(C_1-C_6)$alkyl radical; an N—Z-amino$(C_1-C_6)$alkylcarbonyl$(C_1-C_6)$alkyl radical; an N-$(C_1-C_6)$alkylamino$(C_1-C_6)$alkylcarbonyl$(C_1-C_6)$alkyl radical; an N,N-di$(C_1-C_6)$alkylamino-$(C_1-C_6)$alkylcarbonyl$(C_1-C_6)$alkyl radical; a carboxyl radical; a $(C_1-C_6)$alkylcarboxyl radical; a $(C_1-C_6)$alkylsulphonyl radical; an aminosulphonyl radical; an N—Z-aminosulphonyl radical; an N-$(C_1-C_6)$alkylaminosulphonyl radical; an N,N-di$(C_1-C_6)$alkylaminosulphonyl radical; an aminosulphonyl$(C_1-C_6)$alkyl radical; an N—Z-aminosulphonyl$(C_1-C_6)$alkyl radical; an N-$(C_1-C_6)$alkylaminosulphonyl$(C_1-C_6)$alkyl radical; an N,N-di$(C_1-C_6)$alkylaminosulphonyl$(C_1-C_6)$alkyl radical; a carbamyl radical; an N-$(C_1-C_6)$alkylcarbamyl radical; an N,N-di$(C_1-C_6)$alkylcarbamyl radical; a carbamyl$(C_1-C_6)$alkyl radical; an N-$(C_1-C_6)$alkylcarbamyl ($C_1$–$C_6$)alkyl radical; an N,N-di($C_1$–$C_6$)alkylcarbamyl ($C_1$–$C_6$)alkyl radical; a ($C_1$–$C_6$)alkyl radical; a monohydroxy($C_1$–$C_6$)alkyl radical; a polyhydroxy ($C_2$–$C_6$)alkyl radical; a ($C_1$–$C_6$)alkoxy($C_1$–$C_6$)alkyl radical; a trifluoro($C_1$–$C_6$)alkyl radical; a cyano radical; an $OR^5$ or —$SR^5$ group wherein $R_5$ is as defined below; and an amino($C_1$–$C_6$)alkyl radical, wherein the alkyl is unsubstituted or substituted by one or more hydroxyl radicals and the amine is unsubstituted or substituted by one or two identical or different radicals which may together form, with the nitrogen atom to which they are attached, a carbonaceous 5- or 6-membered ring or a 5- or 6-membered ring comprising one or more heteroatoms, or which are chosen from ($C_1$–$C_6$)alkyl, monohydroxy($C_1$–$C_6$)alkyl, polyhydroxy($C_1$–$C_6$)alkyl, ($C_1$–$C_6$)alkylcarbonyl, carbamyl, N-($C_1$–$C_6$)alkylcarbamyl, N,N-di($C_1$–$C_6$) alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, and from a Z group as defined below;

$R_5$ is chosen from a hydrogen atom; a ($C_1$–$C_6$)alkyl radical; a monohydroxy($C_1$–$C_6$)alkyl radical; a polyhydroxy($C_2$–$C_6$)alkyl radical; a Z group as defined below; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxy($C_1$–$C_6$)alkyl radical; a cyano($C_1$–$C_6$)alkyl radical; a carbamyl($C_1$–$C_6$)alkyl radical; an N-($C_1$–$C_6$)alkylcarbamyl($C_1$–$C_6$)alkyl radical; an N,N-di($C_1$–$C_6$)alkylcarbamyl($C_1$–$C_6$)alkyl radical; a trifluoro($C_1$–$C_6$)alkyl radical; an aminosulphonyl ($C_1$–$C_6$)alkyl radical; an N—Z-aminosulphonyl ($C_1$–$C_6$)alkyl radical; an N-($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$) alkylsulphonyl($C_1$–$C_6$)alkyl radical; a ($C_1$–$C_6$) alkylcarbonyl($C_1$–$C_6$)alkyl radical; an amino($C_1$–$C_6$) alkyl radical, wherein the alkyl is unsubstituted or substituted by one or more hydroxyl radicals; and an amino($C_1$–$C_6$)alkyl radical, wherein the alkyl is unsubstituted or substituted by one or more hydroxyl radicals and the amine is substituted by one or two identical or different radicals which may together form, with the nitrogen atom to which they are attached, a carbonaceous 5- or 6-membered ring or a 5- or 6-membered ring comprising one or more heteroatoms, or which are chosen from ($C_1$–$C_6$)alkyl, monohydroxy($C_1$–$C_6$)alkyl, polyhydroxy($C_2$–$C_6$)alkyl, ($C_1$–$C_6$)alkylcarbonyl, formyl, trifluoro($C_1$–$C_6$)alkylcarbonyl, ($C_1$–$C_6$) alkylcarboxyl, carbamyl, N-($C_1$–$C_6$)alkylcarbamyl, N,N-di($C_1$–$C_6$)alkylcarbamyl, thiocarbamyl and ($C_1$–$C_6$)alkylsulphonyl radicals, and from a Z group as defined below;

Z is chosen from the unsaturated cationic groups of following formulae (II) and (III) and the saturated cationic groups of following formula (IV):

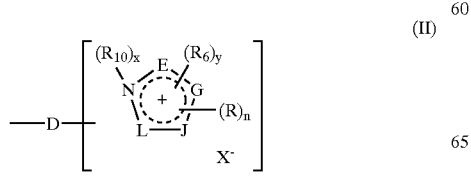
(II)

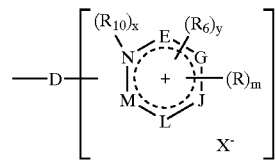
(III)

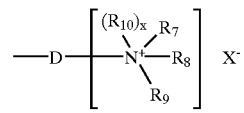
(IV)

wherein:

D is a linking arm which is a linear or branched alkyl chain, which can be interrupted by one or more heteroatoms, can be substituted by one or more hydroxyl or ($C_1$–$C_6$)alkoxy radicals, and can carry one or more ketone functional groups;

the E, G, J, L and M vertices, which are identical or different, are chosen from carbon, oxygen, sulphur and nitrogen atoms;

n is an integer ranging from 0 to 4;

m is an integer ranging from 0 to 5;

the R radicals, which are identical or different, are chosen from a second Z group identical to or different from the first Z group; a halogen atom; a hydroxyl radical; a ($C_1$–$C_6$)alkyl radical; a monohydroxy($C_1$–$C_6$)alkyl radical; a polyhydroxy ($C_2$–$C_6$)alkyl radical; a nitro radical; a cyano radical; a cyano($C_1$–$C_6$)alkyl radical; a ($C_1$–$C_6$)alkoxy radical; a tri($C_1$–$C_6$)alkylsilyl($C_1$–$C_6$)alkyl radical; an amido radical; a formyl radical; a carboxyl radical; a ($C_1$–$C_6$)alkylcarbonyl radical; a thio radical; a thio ($C_1$–$C_6$)alkyl radical; a ($C_1$–$C_6$)alkylthio radical; an amino radical; an amino radical protected by a ($C_1$–$C_6$)alkylcarbonyl, carbamyl or ($C_1$–$C_6$) alkylsulphonyl radical; and an NHR" or NR"R'" group, wherein R" and R'", which are identical or different, are chosen from a ($C_1$–$C_6$)alkyl radical, a monohydroxy($C_1$–$C_6$)alkyl radical and a polyhydroxy($C_2$–$C_6$)alkyl radical;

$R_6$ is chosen from a ($C_1$–$C_6$)alkyl radical; a monohydroxy($C_1$–$C_6$)alkyl radical; a polyhydroxy ($C_2$–$C_6$)alkyl radical; a cyano($C_1$–$C_6$)alkyl radical; a tri($C_1$–$C_6$)alkylsilyl($C_1$–$C_6$)alkyl radical; a($C_1$–$C_6$) alkoxy($C_1$–$C_6$)alkyl radical; a carbamyl($C_1$–$C_6$) alkyl radical; a ($C_1$–$C_6$)alkylcarboxy($C_1$–$C_6$)alkyl radical; a benzyl radical; and a second Z group identical to or different from the first Z group;

$R_7$, $R_8$ and $R_9$, which are identical or different, are chosen from a ($C_1$–$C_6$)alkyl radical; a monohydroxy ($C_1$–$C_6$)alkyl radical; a polyhydroxy($C_2$–$C_6$)alkyl radical; a ($C_1$–$C_6$)alkoxy($C_1$–$C_6$)alkyl radical; a cyano($C_1$–$C_6$)alkyl radical; an aryl radical; a benzyl radical; an amido($C_1$–$C_6$)alkyl radical; a tri($C_1$–$C_6$) alkylsilyl($C_1$–$C_6$)alkyl radical; and an amino($C_1$–$C_6$) alkyl radical, wherein the amine is protected by a ($C_1$–$C_6$)alkylcarbonyl, carbamyl or ($C_1$–$C_6$) alkylsulphonyl radical; or wherein two of the $R_7$, $R_8$ and $R_9$ radicals together form, with the nitrogen atom to which they are attached, a saturated carbonaceous 5- or 6-membered ring or a saturated 5- or 6-membered ring which can comprise one or more heteroatoms, and which can be unsubstituted or substituted by a halogen atom, a hydroxyl radical, a $(C_1-C_6)$alkyl radical, a monohydroxy$(C_1-C_6)$alkyl radical, a polyhydroxy$(C_2-C_6)$alkyl radical, a nitro radical, a cyano radical, a cyano$(C_1-C_6)$alkyl radical, a $(C_1-C_6)$alkoxy radical, a tri$(C_1-C_6)$alkylsilyl$(C_1-C_6)$alkyl radical, an amido radical, a formyl radical, a carboxyl radical, a keto$(C_1-C_6)$alkyl radical, a thio radical, a thio$(C_1-C_6)$alkyl radical, a $(C_1-C_6)$alkylthio radical, an amino radical or an amino radical protected by a $(C_1-C_6)$alkylcarbonyl, carbamyl or $(C_1-C_6)$alkylsulphonyl radical; or wherein one of the $R_7$, $R_8$ and $R_9$ radicals is a second Z group identical to or different from the first Z group;

$R_{10}$ is chosen from a $(C_1-C_6)$alkyl radical; a monohydroxy$(C_1-C_6)$alkyl radical; a polyhydroxy $(C_2-C_6)$alkyl radical; an aryl radical; a benzyl radical; an amino$(C_1-C_6)$alkyl radical; an amino$(C_1-C_6)$alkyl radical, wherein the amine is protected by a $(C_1-C_6)$alkylcarbonyl, carbamyl or $(C_1-C_6)$alkylsulphonyl radical; a carboxy$(C_1-C_6)$alkyl radical; a cyano$(C_1-C_6)$alkyl radical; a carbamyl$(C_1-C_6)$alkyl radical; a trifluoro$(C_1-C_6)$alkyl radical; a tri$(C_1-C_6)$alkylsilyl$(C_1-C_6)$alkyl radical; a sulphonamido$(C_1-C_6)$alkyl radical; a $(C_1-C_6)$alkylcarboxy$(C_1-C_6)$alkyl radical; a $(C_1-C_6)$alkylsulphinyl$(C_1-C_6)$alkyl radical; a $(C_1-C_6)$alkylsulphonyl$(C_1-C_6)$alkyl radical; a $(C_1-C_6)$alkylketo$(C_1-C_6)$alkyl radical; an N-$(C_1-C_6)$alkylcarbamyl$(C_1-C_6)$alkyl radical; and an N-$(C_1-C_6)$alkylsulphonamido$(C_1-C_6)$alkyl radical;

x and y are integers equal to 0 or 1, with the provisos that:
in the unsaturated cationic groups of formula (II):
when x=0, the D linking arm is attached to the nitrogen atom,
when x=1, the D linking arm is attached to one of the E, G, J or L vertices,
y can take the value 1 only when:
1) the E, G, J and L vertices simultaneously represent a carbon atom and when the $R_6$ radical is carried by the nitrogen atom of the unsaturated ring; or
2) at least one of the E, G, J and L vertices represents a nitrogen atom to which the $R_6$ radical is attached;
the unsaturated cationic groups of formula (III):
when x=0, the D linking arm is attached to the nitrogen atom,
when x=1, the D linking arm is attached to one of the E, G, J, L or M vertices,
y can take the value 1 only when at least one of the E, G, J, L and M vertices represents a divalent atom and when the $R_6$ radical is carried by the nitrogen atom of the unsaturated ring;
the cationic groups of formula (IV):
when x=0, the D linking arm is attached to the nitrogen atom carrying the $R_7$, $R_8$ and $R_9$ radicals,
when x=1, two of the $R_7$, $R_8$ and $R_9$ radicals jointly form, with the nitrogen atom to which they are attached, a saturated carbonaceous 5- or 6-membered ring or a saturated 5- or 6-membered ring which can comprise one or more heteroatoms, and which can be unsubstituted or substituted by a halogen atom, a hydroxyl radical, a $(C_1-C_6)$alkyl radical, a monohydroxy$(C_1-C_6)$alkyl radical, a polyhydroxy$(C_1-C_6)$alkyl radical, a nitro radical, a cyano radical, a cyano$(C_1-C_6)$alkyl radical, a $(C_1-C_6)$alkoxy radical, a tri$(C_1-C_6)$alkylsilyl$(C_1-C_6)$alkyl radical, an amido radical, a formyl radical, a carboxyl radical, a keto$(C_1-C_6)$alkyl radical, a thio radical, a thio$(C_1-C_6)$alkyl radical, a $(C_1-C_6)$alkylthio radical, an amino radical or an amino radical protected by a $(C_1-C_6)$alkylcarbonyl, carbamyl or $(C_1-C_6)$alkylsulphonyl radical; and the D linking arm is carried by a carbon atom of the said saturated ring;

$X^-$ represents a monovalent or divalent anion;

provided that: at least one of $R_1$, $R_2$, $R_3$ and $R_4$ comprises at least one Z group of the formula (II), wherein at least one of the E, G, J, and L vertices represents a nitrogen atom; and when one and only one of the $R_1$ or $R_2$ or $R_5$ radicals is a Z group wherein the D linking arm represents an alkyl chain comprising a ketone functional group, then said ketone functional group is not directly attached to the nitrogen atom of the $NR_1R_2$ group or to the oxygen atom of the $OR_5$ group when $R_1$ or $R_2$ is $OR_5$.

18. A process according to claim 17, wherein said keratinous fibers are human keratinous fibers.

19. A process according to claim 18, wherein said human keratinous fibers are hair.

20. A process according to claim 17, wherein said dyeing composition is applied to dry or wet keratinous fibers, and said fibers are dried without intermediate rinsing.

21. A process according to claim 17, wherein said dyeing composition is applied to dry or wet keratinous fibers, and, after said composition is optionally allowed to act on said fibers for an exposure time ranging from 3 to 60 minutes, said fibers are rinsed, optionally washed and rinsed again, and dried.

* * * * *

UNITED STATES PATENT AND TRADEMARK OFFICE
CERTIFICATE OF CORRECTION

PATENT NO. : 6,478,827 B1
DATED : November 12, 2002
INVENTOR(S) : Alain Genet et al.

It is certified that error appears in the above-identified patent and that said Letters Patent is hereby corrected as shown below:

Column 24,
Line 38, "a($C_1$-$C_6$)alkoxy" should read -- a ($C_1$-$C_6$)alkoxy --.
Line 52, "radical;,a" should read -- radical; a --.
Line 61, "a($C_1$-$C_6$)alkoxy($C_1$-$C_6$)alkyl" should read -- a ($C_1$-$C_6$)alkoxy($C_1$-$C_6$)alkyl --.

Column 25,
Lines 30-31, "a($C_1$-$C_6$)alkylcarboxy($C_1$-$C_6$)alkyl" should read -- a ($C_1$-$C_6$)alkylcarboxy($C_1$-$C_6$)alkyl --.

Column 26,
Line 7, before "($C_1$-$C_6$)alkoxy", insert -- a --.

Column 27,
Lines 4-5, "1-{-2-(5-(2-hydroxyethylamino)-2-methyl-4-nitrophenoxy)ethyl}-3-methyl-3H-imidazol-1-ium" should read -- 1-{2-(5-(2-hydroxyethylamino)-2-methyl-4-nitrophenoxy)ethyl}-3-methyl-3H-imidazol-1-ium --.
Lines 38-39, "1-(2-(2-methoxy4-nitrophenylamino)ethyl)-3-methyl-3H-imidazol-1-ium" should read -- 1-(2-(2-methoxy-4-nitrophenylamino)ethyl)-3-methyl-3H-imidazol-1-ium --.

Column 28,
In the structure for formula $(I)_7$ between lines 51-57:
"

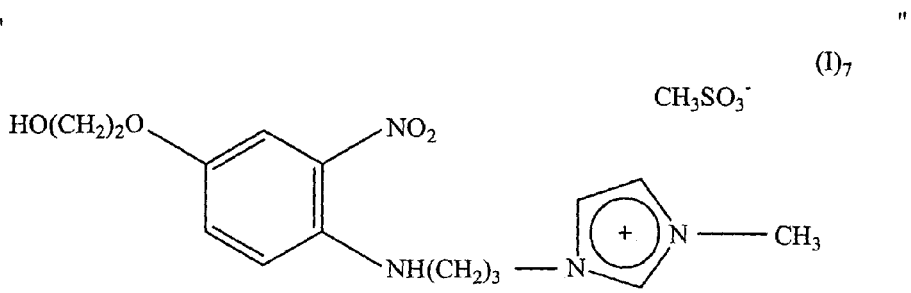

"

should read

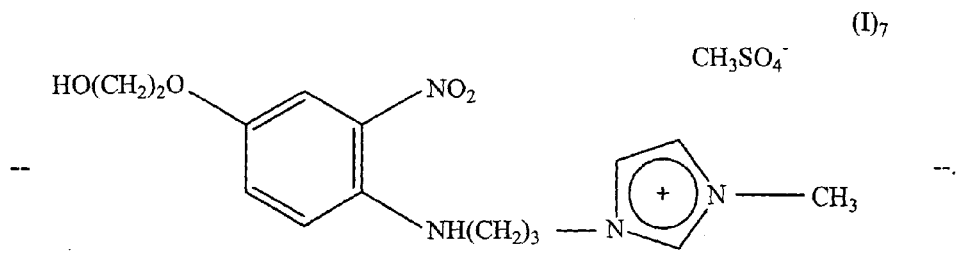

--.

UNITED STATES PATENT AND TRADEMARK OFFICE
CERTIFICATE OF CORRECTION

PATENT NO. : 6,478,827 B1
DATED : November 12, 2002
INVENTOR(S) : Alain Genet et al.

It is certified that error appears in the above-identified patent and that said Letters Patent is hereby corrected as shown below:

Column 28 (cont'd),
In the structure for formula $(I)_8$ between lines 58-67:

"
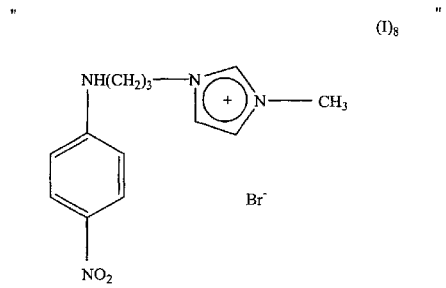
"

should read

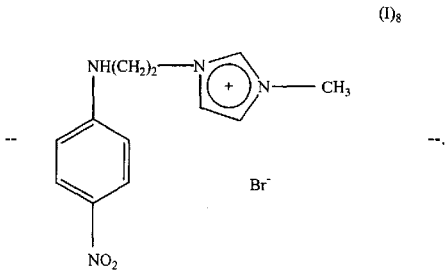

-- --.

Column 29,
In the structure for formula $(I)_{11}$ between lines 19-28:

"
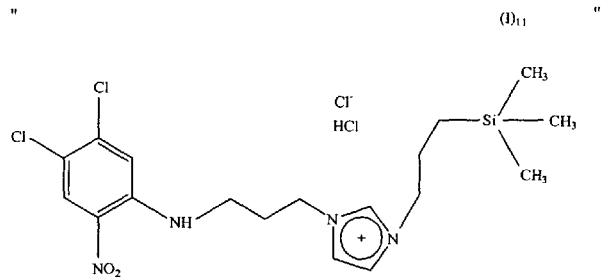
"

should read

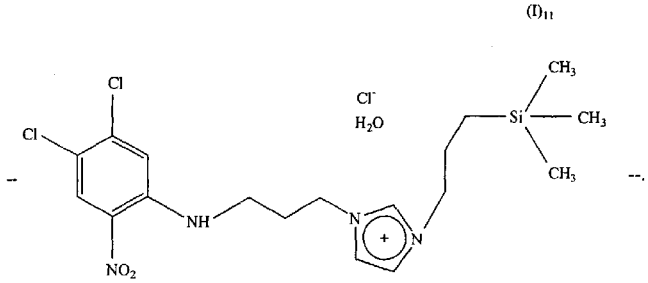

-- --.

UNITED STATES PATENT AND TRADEMARK OFFICE
CERTIFICATE OF CORRECTION

PATENT NO.    : 6,478,827 B1
DATED         : November 12, 2002
INVENTOR(S)   : Alain Genet et al.

It is certified that error appears in the above-identified patent and that said Letters Patent is hereby corrected as shown below:

Column 31,
Line 15, "from($C_1$-$C_6$)alkyl," should read -- from ($C_1$-$C_6$)alkyl, --.

Column 32,
Lines 47-48, "a($C_1$-$C_6$)alkoxy($C_1$-$C_6$alkyl" should read -- a ($C_1$-$C_6$)alkoxy($C_1$-$C_6$)alkyl --

Signed and Sealed this

Seventeenth Day of June, 2003

JAMES E. ROGAN
*Director of the United States Patent and Trademark Office*